(12) United States Patent  
Coelho et al.

(10) Patent No.: US 9,821,111 B2  
(45) Date of Patent: Nov. 21, 2017

(54) CELL SEPARATION DEVICES, SYSTEMS, AND METHODS

(71) Applicant: SynGen Inc., Sacramento, CA (US)

(72) Inventors: Philip H. Coelho, Sacramento, CA (US); William Busa, Sacramento, CA (US); Jonathan Ellis, Sacramento, CA (US)

(73) Assignee: ThermoGenesis Corporation, Rancho Cordova, CA (US)

( * ) Notice: Subject to any disclaimer, the term of this patent is extended or adjusted under 35 U.S.C. 154(b) by 0 days.

(21) Appl. No.: 15/489,968

(22) Filed: Apr. 18, 2017

(65) Prior Publication Data

US 2017/0224904 A1 Aug. 10, 2017

Related U.S. Application Data

(62) Division of application No. 15/393,628, filed on Dec. 29, 2016, now Pat. No. 9,695,394.

(60) Provisional application No. 62/272,533, filed on Dec. 29, 2015.

(51) Int. Cl.
- *G01N 33/58* (2006.01)
- *A61M 1/36* (2006.01)
- *C12N 5/078* (2010.01)

(52) U.S. Cl.
CPC ......... *A61M 1/3693* (2013.01); *C12N 5/0634* (2013.01)

(58) Field of Classification Search
CPC .................................................. G01N 33/585
See application file for complete search history.

(56) References Cited

U.S. PATENT DOCUMENTS

| | | |
|---|---|---|
| 3,211,368 A | 10/1965 | Shanley et al. |
| 4,332,351 A | 6/1982 | Kellogg et al. |
| 4,482,342 A | 11/1984 | Lueptow et al. |
| 4,608,178 A | 8/1986 | Johansson et al. |
| 4,636,193 A | 1/1987 | Cullis |
| 4,850,995 A | 7/1989 | Tie et al. |
| 5,116,724 A | 5/1992 | Delaage et al. |
| 7,211,191 B2 | 5/2007 | Coelho et al. |
| 8,747,289 B2 | 6/2014 | Coelho |
| 9,260,697 B2 | 2/2016 | Cimino et al. |
| 9,574,165 B2 | 2/2017 | Wada et al. |
| 2001/0009757 A1 | 7/2001 | Bischof et al. |
| 2001/0034435 A1 | 10/2001 | Nochumson et al. |
| 2003/0104359 A1 | 6/2003 | Cuthbertson et al. |
| 2007/0036722 A1 | 2/2007 | Rongved et al. |
| 2007/0151933 A1 | 7/2007 | Coelho et al. |
| 2009/0176201 A1 | 7/2009 | Jablonski et al. |

(Continued)

FOREIGN PATENT DOCUMENTS

| | | |
|---|---|---|
| WO | 2009/052057 | 4/2009 |
| WO | 2015/148390 A1 | 10/2015 |

OTHER PUBLICATIONS

Diamandis et al., The Biotin-(Stept) Avidin System: Principles and Applications in Biotechnology, Clin. Chem., 1991, pp. 625-636, vol. 37., No. 5.

(Continued)

*Primary Examiner* — Rosanne Kosson  
(74) *Attorney, Agent, or Firm* — McDonnell Boehnen Hulbert & Berghoff LLP

(57) ABSTRACT

Disclosed herein are cell separation devices, methods and systems, as well as compositions and reagents for use in cell separation methods.

27 Claims, 12 Drawing Sheets

(56) References Cited

U.S. PATENT DOCUMENTS

| | | |
|---|---|---|
| 2012/0003733 A1 | 1/2012 | Gueneron |
| 2013/0029370 A1 | 1/2013 | Coelho |
| 2013/0164731 A1 | 6/2013 | Cimino et al. |
| 2013/0210600 A1 | 8/2013 | Chapman et al. |
| 2015/0219636 A1 | 8/2015 | Rychak et al. |
| 2016/0144382 A1 | 5/2016 | Riera-Domenech |
| 2016/0208211 A1 | 7/2016 | Cimino et al. |

OTHER PUBLICATIONS

Hsu et al., "Fast Sorting of CD4+ T cells from Whole Blood Using Glass Microbubbles," Technology, Mar. 2015, pp. 38-44, vol. 3, No. 1.

Hsu et al., "Isolating Cells from Blood Using Buoyancy Activated Cell Sorting (BACS) with Glass Microbubbles," 14th International Conference on Miniaturized Systems for Chemistry and Life Sciences, Oct. 3-7, 2010, Groningen, The Netherlands, pp. 3-7.

Liou et al., "Buoyancy-activated Cell Sorting Using Targeted Biotinylated Albumin Microbubbles," PLoS One, May 2015, e0125036, vol. 10, No. 5.

Shi et al., "Binding and Isolation of Tumor Cells in Biological Media with Perfluorocarbon Microbubbles," Methods, 2013, pp. 102-107, vol. 64, No. 2.

Shi et al., "Isolation of Rare Tumor Cells from Blood Cells with Buoyant Immuno-Microbubbles," PLoS One, 2013, e58017, vol. 8, No. 3.

Stefannson et al., "Isolation of Low Abundance Proteins and Cells Using Buoyant Glass Microbubble Chromatography," Chromatography Research International, 2013, Article ID 341036, 6 pages.

International Search Report for PCT/US2016/069115, dated Jun. 28, 2017.

| ID | SOURCE MATERIAL | PRE-PROCESSING DEPLETION | BACS Protocol | PRE-BACS WBC CONC. (10⁶/mL) | BACS PROCESS VOL (mL) | UNBOUND WASH STEP? | OLIGONUCLEOTIDE LINKER | TARGET | TARGET CELLS (% OF TOTAL) | MICROBUBBLE DIAM. (APPROX, μm) | MICROBUBBLE VENDOR | TARGET CELL RECOVERY (%) | TARGET CELL PURITY (%) | TARGET CELL VIABILITY (%) |
|---|---|---|---|---|---|---|---|---|---|---|---|---|---|---|
| 8 | PERIPHERAL BLOOD | RBC/PLT/GRN (SYNGENX-LAB) | Small Scale, open process | 9.8 | 1 | NO | 8-MER | CD3 | 1.2 | 4.5 | B | 12.5 | 99.3 | 98.5 |
| 9 | PERIPHERAL BLOOD | RBC/PLT/GRN (SYNGENX-LAB) | Small Scale, open process | 9.8 | 1 | NO | 10-MER | CD3 | 1.2 | 4.5 | B | 21.7 | 98.7 | 98.9 |
| 10 | PERIPHERAL BLOOD | RBC/PLT/GRN (SYNGENX-LAB) | Small Scale, open process | 9.8 | 1 | NO | 12-MER | CD3 | 1.2 | 4.5 | B | 68.4 | 99.6 | 98.9 |
| 11 | PERIPHERAL BLOOD | RBC/PLT/GRN (SYNGENX-LAB) | Small Scale, open process | 9.8 | 1 | NO | 14-MER | CD3 | 1.2 | 4.5 | B | 78.2 | 99.1 | 98.8 |
| 12 | PERIPHERAL BLOOD | RBC/PLT/GRN (SYNGENX-LAB) | Large Scale, closed process | 12.5 | 45 | NO | 14-MER | CD3 | 2.0 | 4.5 | B | 76.7 | 97.3 | 96.8 |
| 16 | PERIPHERAL BLOOD | RBC/PLT/GRN (SYNGENX-LAB) | Small Scale, open process | 7.5 | 3 | NO | 14-MER | CD3 | 1.4 | 2.0 | C | 94.5 | 99.1 | 93.8 |

Figure 11

| ID | SOURCE MATERIAL | PRE-PROCESSING DEPLETION | BACS Protocol | PRE-BACS WBC CONC. (10⁶/mL) | BACS PROCESS VOL (mL) | UNBOUND WASH STEP? | OLIGONUCLEOTIDE LINKER | TARGET | TARGET CELLS (% OF TOTAL) | MICROBUBBLE DIAM. (APPROX. µm) | MICROBUBBLE VENDOR | TARGET CELL RECOVERY (%) | TARGET CELL PURITY (%) | TARGET CELL VIABILITY (%) |
|---|---|---|---|---|---|---|---|---|---|---|---|---|---|---|
| 1 | PERIPHERAL BLOOD | RBC/PLT/GRN (SYNGENX-LAB) | Large Scale, closed process | 14.5 | 45 | NO | NONE | CD3 | 2.2 | 2.5 | A | 80.9 | 99.6 | 92.2 |
| 2 | PERIPHERAL BLOOD | RBC/PLT/GRN (SYNGENX-LAB) | Large Scale, closed process | 19.4 | 45 | NO | NONE | CD3 | 2.8 | 2.5 | A | 88.1 | 98.2 | 95.8 |
| 3 | PERIPHERAL BLOOD | RBC/PLT/GRN (SYNGENX-LAB) | Large Scale, closed process | 14.5 | 45 | NO | NONE | CD3 | 0.7 | 2.5 | A | 84.5 | 94.8 | 90.7 |
| 4 | PERIPHERAL BLOOD | RBC/PLT/GRN (SYNGENX-LAB) | Large Scale, closed process | 13.4 | 41 | NO | NONE | CD3 | 1.5 | 2.5 | A | 86.9 | 96.6 | 92.2 |
| 5 | PERIPHERAL BLOOD | RBC/PLT/GRN (SYNGENX-LAB) | Large Scale, closed process | 10.6 | 45 | NO | NONE | CD3 | 2.1 | 3.5 | B | 88.4 | 92.1 | 93.6 |
| 6 | PERIPHERAL BLOOD | NONE | Large Scale, closed process | 5.7 | 200 | NO | NONE | CD3 | 0.034 | 2.5 | A | 77.3 | 94.8 | 94.8 |
| 7 | PERIPHERAL BLOOD | NONE | Large Scale, closed process | 5.1 | 200 | NO | NONE | CD3 | 0.031 | 2.5 | A | 68.4 | 93.9 | 97.0 |
| 12 | PERIPHERAL BLOOD | RBC/PLT/GRN (SYNGENX-LAB) | Large Scale, closed process | 12.5 | 45 | NO | 14-MER | CD3 | 2.0 | 4.5 | B | 76.7 | 97.3 | 96.8 |
| 13 | PERIPHERAL BLOOD | RBC/PLT/GRN (SYNGENX-LAB) | Small Scale, open process | 10.2 | 10 | NO | NONE | CD4 | 2.3 | 2.5 | A | 78.1 | 93.2 | 90.1 |
| 14 | PERIPHERAL BLOOD | RBC/PLT/GRN (SYNGENX-LAB) | Large Scale, closed process | 17.7 | 45 | NO | NONE | CD4 | 1.4 | 2.5 | A | 81.7 | 96.6 | 95.3 |
| 15 | PERIPHERAL BLOOD | RBC/PLT/GRN (SYNGENX-LAB) | Small Scale, open process | 11.1 | 10 | NO | NONE | CD19 | 0.4 | 2.5 | A | 78.3 | 94.2 | 94.1 |
| 20 | LEUKAPHERESIS | PLT (SYNGENX-LAB) RBC/PLT/GRN | Large Scale, closed process | 55.2 | 75 | NO | NONE | CD3 | 16.3 | 4.5 | B | 83.0 | 98.6 | 96.1 |
| 23 | CORD BLOOD | (SYNGENX-LAB) RBC/PLT/GRN | Small Scale, open process | 10.3 | 10 | NO | NONE | CD3 | 2.1 | 4.5 | B | 79.1 | 98.3 | 94.9 |
| 24 | CORD BLOOD | (SYNGENX-LAB) RBC/PLT/GRN | Small Scale, open process | 23.2 | 20 | NO | NONE | CD3 | 2.3 | 4.5 | B | 81.4 | 97.2 | 95.7 |
| 26 | CORD BLOOD | (SYNGENX-LAB) RBC/PLT/GRN | Small Scale, open process | 11.3 | 10 | NO | NONE | CD4 | 1.4 | 2.5 | A | 80.1 | 92.1 | 90.2 |
| 34 | BONE MARROW | (SYNGENX-LAB) | Large Scale, open process | 21.1 | 15.1 | No | 14-MER Depletion (%) | CD34 | 0.10% | 4.5 | B | 74.3 | 97.7 | 100 |
| 36 | PERIPHERAL BLOOD | NONE | Small Scale, open process | 24.1 | 25 | NO | NONE | CD235a | 48.2 | 2.5 | A | | >99 | |
| 37 | PERIPHERAL BLOOD | NONE | Small Scale, open process | 22.6 | 25 | NO | NONE | CD235a | 53.6 | 3.5 | B | | 98.2 | |
| 38 | CORD BLOOD | NONE | Small Scale, open process | 37.3 | 20 | NO | NONE | CD235a | 43.5 | 2.5 | B | | 99.1 | |

Figure 12

CELL SEPARATION DEVICES, SYSTEMS, AND METHODS

RELATED APPLICATIONS

This application is a divisional of U.S. application Ser. No. 15/393,628 filed Dec. 29, 2016, which claims priority to U.S. Provisional Application No. 62/272,533 filed on Dec. 29, 2015, which is hereby incorporated by reference in its entirety.

BACKGROUND OF THE DISCLOSURE

Recent clinical trials establish that certain rare stem, progenitor or immune cell populations have clinical utility in regenerative medicine and immunotherapy (references). Such rare target cells may be as much as five orders of magnitude ($10^5$) less numerous than the other cells in blood or bone marrow, the most numerous of which are red blood cells and platelets. The admixture of abundant unwanted cells with rare, clinically important target cells presents a challenge in enriching and purifying the target cells. The major cell populations in blood and bone marrow differ in size and density, so that stratifying cells based on their densities during centrifugation can be utilized in the selection and purification process. For example, normal human blood generally comprises red blood cells ("RBCs"), the most numerous and most dense cell; platelets ("PLTs"), the smallest and least dense cell; white blood cells ("WBCs"), the largest cells, with a density between the RBCs and the PLTs, and plasma. These three cell fractions separate into distinct populations during centrifugation. On average, RBCs make up approximately 99.9% of an individual's total blood cells and approximately 45% of the total volume of blood within an individual, although this is known to vary among individuals and, over time, within the same individual. RBCs serve a vital function as the principal means of delivering oxygen to body tissues, but are not useful for regenerating tissue or enhancing the immune system to combat certain diseases, including cancers. Nearly all of the remainder of an individual's blood volume is made up of plasma, a non-cellular liquid accounting for approximately 55% of the total blood volume and in which all blood cells are suspended. Thus, over 99% of the volume of normal blood is made up of plasma and RBCs.

The remaining approximately <0.6% of the volume of normal blood consists of WBCs and Platelets (PLTs). PLTs are small, irregularly shaped anuclear cells that outnumber the WBCs by a factor of ~30 times. PLTs play a fundamental role in hemostasis and healing by stopping bleeding and releasing a multitude of growth factors that repair and regenerate damaged tissue. However, their adhesive nature interferes with the efficient enrichment and purification of the rare, clinically important target cells. The least prevalent blood cells are WBCs, making up only about one tenth of one percent of the total cells in a typical blood sample. WBCs are critical to the body's immune system, and participate in the defense of the body against infectious disease, foreign materials and hematologic and solid tumor cancers. Nearly all of the cells that are utilized clinically in immunotherapy or regenerative medicine reside within the WBC fraction. WBCs may be further divided into subgroups. The largest and most dense subgroup is the granulocytes (GRNs), which make up approximately 60% of all WBCs. The smaller and less dense subgroup are the mononuclear cells (MNCs), which constitute the remaining approximately 40%. MNCs can further be broken down into lymphocytes and monocytes, but they are collectively referred to as MNCs due to the presence in each cell of a single round nucleus. MNCs are critical elements of the immune system, comprising T cells, B cells and NK cells that migrate to sites of infection in body tissue and then divide and differentiate into macrophages and dendritic cells to elicit an immune response. Many cell therapies now being explored in clinical trials utilize cells that reside within the MNC fraction.

Thus, in order to purify a rare population of cells from blood, bone marrow or leukapheresis, an initial bulk depletion step to remove substantially all of the much more numerous RBCs, GRNs and PLTs to create an enriched MNC fraction is desirable. As previously mentioned, this can be accomplished using centrifugation. Centrifugation is a method of cell processing classified by the FDA as "minimally manipulated", which provides a simpler regulatory path for FDA clearance. Performing this initial bulk depletion process alone on blood can enrich the rare cell populations residing in the MNC fraction by three orders of magnitude ($10^3$), which makes subsequent additional purification and enrichment of the target cells more efficient.

Current methods for isolating target cells begins with a manual method of isolating MNCs require a highly skilled operator working with density gradient mediums, such as Ficoll. Density gradient mediums are small particles of a precise density intermediate to, for instance, the density of granulocytes and MNCs so that when combined and centrifuged, the particles stratify and interpose their layer in between the granulocyte layer and the MNC layer making the subsequent pipette retrieval of the MNCs without the presence of granulocytes more attainable. Subsequent purification to the final target cells within the MNCs requires expensive and complex instrumentation and expensive reagents. These current methods also have low rates of throughput that are unsuitable for purifying rare cells admixed with large quantities of unwanted cells, or have low efficiency of target cell isolation and harvest. These methods may also expose the cells to chemical agents that may have undesirable effects on the cells, or require the use of functionally open systems that present the risk of microbiological contamination of the cells. Therefore, new technologies are needed to enable the isolation, separation, purification, or exchange of medium in which rare cells are suspended with high efficiency, high throughput, and little or no manual intervention, while employing simple equipment, cell-compatible reagents, and functionally closed, sterile systems.

SUMMARY OF THE INVENTION

The present invention provides an apparatus and method for enriching and/or purifying essentially any or all the desired cells residing in a host liquid, including rare desired cells such as stem, progenitor or immune cells, while maintaining viability of the cells under aseptic conditions. The practice of this invention on volumes of cell types exemplified by blood, bone marrow or leukapheresis, which contain clinically relevant numbers of stem, progenitor or immune cells, can provide compositions of target cells that are significantly higher in recovery, viability and purity than can be obtained by all other known devices.

Thus, in a first aspect, the invention provides a cell separation system, comprising:
  (a) a cartridge comprising
    (i) a processing container comprising at least one input port, a first exit port, and a second exit port;
    (ii) a second container comprising an input port;

(iii) a third container comprising an input port and a first exit port;

(iv) a first conduit connecting the first exit port of the processing container and the input port of the second container, wherein the first conduit comprises a first reversible closing device, wherein the second container is transiently fluidically connected to the processing container such that fluid flow only from the processing container to the second container may occur when the first reversible closing device is opened;

(v) a second conduit connecting the second exit port of the processing container and the input port of the third container, wherein the second conduit comprises a second reversible closing device, wherein the third container is transiently fluidically connected to the processing container such that fluid flow only from the processing container to the third container may occur when the second reversible closing device is opened;

(b) a transfer container comprising at least one port;

(c) an at least third conduit connecting (i) the first exit port of the third container to the at least one port of the transfer container, and (ii) the at least one port of the transfer container to the at least one input port of the processing container wherein the at least third conduit comprises at least a third reversible closing device, such that (A) the third container is transiently fluidically connected to the transfer container, and (B) the transfer container is transiently fluidically connected to the processing container; wherein the at least third conduit is configured such that only one of the following may be true (I) fluid flow only from the third container to the transfer container may occur when the at least third reversible closing device is opened; or (II) fluid flow only from the transfer container to the processing container may occur when the at least third reversible closing device is opened; and (d) a control module configured to control activity in at least the cartridge, and the first and second conduits.

In one embodiment, the transfer container is internal to the cartridge. In another embodiment, the at least third conduit comprises a single conduit. In another embodiment, the at least third conduit comprises T or Y connector disposed between the third container and transfer container and between the transfer container and the processing container.

In one embodiment, the at least one port of the transfer container comprises a first input port and an exit port. In such an embodiment, the at least third conduit comprises:

(i) a third conduit connecting the exit port of the third container to the input port of the transfer container, wherein the third conduit comprises a third reversible closing device, such that the third container is transiently fluidically connected to the transfer container such that fluid flow only from the third container to the transfer container may occur when the third reversible closing device is opened; and (ii) a fourth conduit connecting the exit port of the transfer container to the at least one input port of the processing container, wherein the fourth conduit comprises a fourth reversible closing device, such that the transfer container is transiently fluidically connected to the processing container, such that fluid flow only from the transfer container to the processing container may occur when the fourth reversible closing device is opened.

In a further embodiment, the at least one input port of the processing container comprises a first input port and a second input port, wherein the at least third conduit, or the fourth conduit (when present), connects the exit port of the transfer container to the first input port of the processing container. In such an embodiment, the cell separation system may further comprise a first medium input conduit connecting the second input port of the processing container to at least one medium reservoir, wherein the first medium input conduit comprises at least a fifth reversible closing device, wherein the at least one medium reservoir is transiently fluidically connected to the processing container such that fluid flow only from the at least one medium reservoir to the processing container may occur when the at least fifth reversible closing device is opened.

In one embodiment, the at least one port of the transfer container further comprises a second input port. In such an embodiment, the cell separation system may further comprise a second medium input conduit connecting the second input port of the transfer container to at least one medium reservoir, wherein the second medium input conduit comprises at least a sixth reversible closing device, wherein the at least one medium reservoir is transiently fluidically connected to the processing container such that fluid flow only from the at least one medium reservoir to the transfer container may occur when the at least sixth reversible closing device is opened.

In one embodiment, the cell separation system further comprises a mixer. In one particular example, the mixer comprises a static mixer. In a further embodiment, the mixer comprises an impeller disposed on an internal surface of a roof of the cartridge. In another embodiment, the mixer comprises an impeller spaced away from an internal surface of a roof of the cartridge. In another embodiment, the mixer comprises a peristaltic pump comprising a pump conduit having a first end and a second end, wherein the first end of the pump conduit is positioned in the processing chamber, and wherein the second end of the pump conduit is positioned outside of the processing chamber and is connected to the at least one input port of the processing chamber. In yet another embodiment, the mixer comprises a mixing module comprising a bottom portion and a top portion, wherein the cartridge is configured to be positioned in the bottom portion, and wherein the top portion is configured to be removably coupled to the bottom portion. In such an embodiment, the mixing module may include a rotatable component coupled to the bottom portion, such that the rotatable component is configured to rotate the cartridge on its vertical axis by 180 degrees or by 360 degrees. In another embodiment, the mixing module may be configured to increase a temperature of the cartridge when the cartridge is positioned in the bottom portion of the mixing module.

In one embodiment, the first medium input conduit and/or the second medium input conduit further comprise a filter. In another embodiment, the second container comprises an exit port coupled to a first waste conduit. In a further embodiment, the processing container further comprises a sterile vent coupled to a second waste conduit.

In another aspect, the invention provides cell separation methods, comprising:

(a) processing a host liquid having a volume of at least 10 mL (or, alternatively, at least 25 mL, at least 50 mL, at least 75 mL, at least 100 mL, at least 200 mL) in a functionally closed system, wherein the host liquid comprises (i) target cells, and (ii) buoyant reagents, wherein the processing comprises contacting the target cells and buoyant reagents for a time and under conditions suitable to promote attachment of the cells to one or more of the buoyant reagents to generate attached target cells;

(b) applying a vectorial force, such as centrifugation, to the host liquid within the functionally closed system to cause the attached target cells to stratify within the host liquid; and (c) sequestering the attached target cells to an area within the functionally closed system.

In one embodiment, the buoyant reagents comprise manufactured buoyant reagents, wherein each manufactured buoyant reagent comprises a buoyant reagent wherein the buoyant label and a binding agent are attached to each other to form the manufactured buoyant reagent prior to contacting the target cells in the host liquid. In another embodiment, the buoyant reagents comprise secondary buoyant reagents that assemble within the host liquid, wherein the method further comprises a preprocessing step, prior to step (a), wherein the preprocessing step comprises contacting the host liquid with buoyant labels and binding agents for a time and under conditions suitable to promote attachment of the binding agents to the buoyant labels to produce the buoyant reagents.

In one embodiment, each buoyant label comprises (i) each binding agent comprises (A) a primary binding agent comprising an agent capable of binding to at least one cellular epitope on the target cells, (B) a first linker bound to the primary binding agent, wherein the first linker comprises a first oligonucleotide having a first complementary region;

(ii) each buoyant label comprises a second linker bound to the buoyant label;

wherein the second linker comprises a second oligonucleotide having a second complementary region, wherein the second complementary region is perfectly complementary to the first complementary region, and wherein a hybrid of the first and second complementary regions has a calculated Tm of at least 40° C.;

wherein the preprocessing step comprises contacting the host liquid with the buoyant labels and the binding agents for a time and under conditions suitable to promote hybridization of the first and second complementary regions to produce the buoyant reagents;

wherein the processing comprises contacting the target cells and the buoyant reagents in the host liquid under conditions suitable to generate the attached target cells; and wherein the method further comprises (d) subjecting the attached target cells to a temperature of 37° C. or less within the functionally closed system after step (c) for a time sufficient to dehybridize the first complementary region and the second complementary region to release the buoyant reagents from the target cells.

In another aspect, the invention provides cell separation methods, comprising:

(a) providing a host liquid, wherein the host liquid comprises attached target cells, wherein each attached target cell comprises (i) a binding agent bound to at least one cellular epitope on a target cell, (ii) a first linker bound to the agent, wherein the first linker comprises a first oligonucleotide having a first complementary region;

(iii) a buoyant label comprising a second linker bound to the buoyant label, wherein the second linker comprises a second oligonucleotide having a second complementary region, wherein the second complementary region is perfectly complementary to the first complementary region, wherein the second complementary region is hybridized to the first complementary region to form a hybrid, and wherein the hybrid of the first and second complementary regions has a calculated Tm of at least 40° C.;

(b) applying a vectorial force, such as centrifugation, to the host liquid to cause the attached target cells to stratify within the host liquid;

(c) sequestering the attached target cells; and (d) subjecting the attached target cells to a temperature of 37° C. or less after step (c) for a time sufficient to dehybridize the first complementary region and the second complementary region to release the buoyant labels from the target cells.

In one embodiment, the attached target cells are generated prior to step (a) by processing steps comprising contacting target cells in the host liquid with manufactured buoyant reagents comprising the binding agent, the first linker, and the second linker, wherein the second complementary region is hybridized to the first complementary region to form the hybrid; wherein the contacting is carried out for a time and under conditions suitable to promote attachment of the cells to one or more of the manufactured buoyant reagents to generate the attached target cells. In another embodiment, the attached target cells are generated prior to step (a) by processing steps comprising: (A) contacting the host liquid with the buoyant labels and binding agents bound to the first linker for a time and under conditions suitable to promote hybridization of the first and second complementary regions to produce buoyant reagents; and (B) contacting the target cells and the buoyant reagents in the host liquid for a time and under conditions suitable to generate the attached target cells.

In either of these aspects the calculated Tm may be the Tm as calculated using the nearest-neighbor two-state model:

$$Tm(°C.) = \frac{\Delta H°}{\Delta S° + R\ln[oligo]} - 273.15$$

where $\Delta H°$ (enthalpy) and $\Delta S°$ (entropy) are the melting parameters calculated from the sequence and the published nearest neighbor thermodynamic parameters and under the ionic conditions used, R is the ideal gas constant (1.987 calK$^{-1}$ mole$^{-1}$), [oligo] is the molar concentration of an oligonucleotide, and the constant of −273.15 converts temperature from Kelvin to degrees of Celsius. In one embodiment, the calculated Tm of the hybrid between the first complementary region and the second complementary region is between 40° C. and about 60° C.

In another embodiment of any of the methods of the invention, the binding agents bind to a cellular epitope on the target cells. In another embodiment, each buoyant reagent comprises one or more second linkers, wherein the one or more second linkers are bound to one or more first linkers attached to at least one binding agent, wherein the at least one binding agent is capable binding to a cellular epitope on the target cell; and wherein the contacting comprises contacting the target cells and the buoyant reagents for a time and under conditions suitable to promote attachment of the target cells to one or more of the buoyant reagents to generate the attached target cells. In another embodiment, the processing may comprise (i) contacting the host liquid with primary binding agents, wherein each primary binding agent comprises (A) an agent capable of binding to at least one cellular epitope on the target cells, and (B) a first linker bound to the agent; wherein the contacting occurs under conditions suitable to promote attachment of the target cells to the primary binding agents to produce target cell-binding agent complexes; and (ii) incubating the target cell-binding agent complexes with the buoyant labels, wherein each buoyant label comprises a second linker, wherein the second linker is capable of binding to the first linker; wherein the incubating occurs under conditions suitable to promote binding of the first linker to the second linker to generate the attached target cells. In one embodiment, no intermediate step of removing unbound primary binding agents occurs between steps (i) and (ii).

In a further embodiment, the methods of the invention may further comprise detaching the buoyant label from the target cells within the functionally closed system to produce detached target cells. In one embodiment of the methods of the invention, the target cells are the desired cells, and the methods may comprise further steps of concentrating the desired cells after sequestration and producing the detached target cells.

In another embodiment of the methods of the invention, the target cells and/or the desired cells may be selected from the group consisting of tumor cells, cancer stem cells, hematopoietic stem and progenitor cells, mesenchymal stem and progenitor cells, adipose-derived stem and progenitor cells, endothelial progenitor cells found in normal blood, placental/cord blood, bone marrow, white blood cells, granulocytes, mononuclear cells, lymphocytes, monocytes, T-cells, B-cells, NK cells, the stromal vascular fraction cells resident in adipose tissue, cultured cells, genetically modified cells, and sub-populations of such target cells. In a specific embodiment, the target cells and/or the desired cells may be selected from the group consisting of CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells.

In various further embodiments of the methods of the invention, the target cells and/or the desired cells represent less than 10%, 5%, 4%, 3%, 2%, or 1% of the cells in non-depleted host liquid. In various further embodiments, a recovery efficiency of the desired cells is greater than 68%, or greater than 75%, or greater than 80%, or greater than 85%, or greater than 90%, or greater than 95%. In other embodiments, viability of the isolated desired cells is greater than 90%, or greater than 95%, or greater than 97%, or greater than 99%. In further embodiments, the target cells and/or desired cells are present at less than 20%, 10%, 5%, 4%, 3%, 2%, or 1% of total cells in the host liquid.

In one embodiment of the methods of the invention, the binding agents may be selected from the group consisting of antibodies, oligonucleotides, aptamers, molecularly imprinted polymers, carbohydrates, proteins, peptides, enzymes, small molecules, lipids, fatty acids, metal atoms, metal ions or synthetic polymers. In a specific embodiment, the binding agents comprise antibodies. In other embodiments, the first linker and second linkers may comprise biotin, avidin, streptavidin, oligonucleotides, antibody-binding proteins, and/or moieties bound by an antibody-binding protein or any second attached binding agent. In specific embodiments, the first linker and second linkers comprise biotin and/or streptavidin, either alone or combined with oligonucleotides.

In another embodiment of the methods of the invention, the buoyant labels may be selected from the group consisting of gas-filled bubbles, hollow polymers, glass beads, microporous beads with entrained gas, droplets of an immiscible liquid, gold nanoparticles, and silver nanoparticles. In a specific embodiment, the buoyant labels comprise gas-filled bubbles. In a further specific embodiment, the gas-filled bubbles comprise perfluorocarbon gas cores encompassed by lipid, phospholipid, carbohydrate or protein shells. In a further specific embodiment, the gas-filled bubbles comprise perfluorocarbon gas cores encompassed by a phospholipid shell. In another specific embodiment, the gas-filled bubbles may have a diameter between about 1 um and about 6.5 um. In a further specific embodiment, the host liquid may be peripheral blood, cord blood, or leukapheresis.

In one embodiment, the functionally closed system for use in the methods of the invention comprises a cell separation system comprising
  (a) a cartridge comprising
    (i) a processing container comprising at least one input port, a first exit port, and a second exit port;
    (ii) two or more additional containers, comprising at least a second container comprising an input port; and a third container comprising an input port and a first exit port;
    (ii) a first conduit connecting the first exit port of the processing container and the input port of the second container, wherein the first conduit comprises a first reversible closing device, wherein the second container is transiently fluidically connected to the processing container such that fluid flow only from the processing container to the second container may occur when the first reversible closing device is opened;
    (v) a second conduit connecting the second exit port of the processing container and the input port of the third container, wherein the second conduit comprises a second reversible closing device, wherein the third container is transiently fluidically connected to the processing container such that fluid flow only from the processing container to the third container may occur when the second reversible closing device is opened;
  (b) a transfer container comprising at least one port;
  (c) an at least third conduit connecting
    (i) the first exit port of the third container to the at least one port of the transfer container, and
    (ii) the at least one port of the transfer container to the at least one input port of the processing container
  wherein the at least third conduit comprises at least a third reversible closing device, such that (A) the third container is transiently fluidically connected to the transfer container, and (B) the transfer container is transiently fluidically connected to the processing container; wherein the at least third conduit is configured such that only one of the following may be true
    (I) fluid flow only from the third container to the transfer container may occur when the at least third reversible closing device is opened; or
    (II) fluid flow only from the transfer container to the processing container may occur when the at least third reversible closing device is opened.

In another embodiment of the methods of the invention, the host liquid to be processed is a depleted host liquid, and prior to the processing or the preprocessing steps, the method comprises applying a vectorial force, such as centrifugation, to non-depleted host liquid within the functionally closed system, such as within the processing container, to deplete non-desired cells, such as by passing the non-desired cells into the second container, thus producing the depleted host liquid to be processed. In a further embodiment, the depleted host liquid is passed from the processing container to the transfer container and mixed with the buoyant reagents to initiate processing the host liquid. In one embodiment, the target cells are the desired cells, and wherein the sequestering comprises passing the detached target cells to the third container. In another embodiment, the target cells are not the desired cells, and the sequestering comprises concentrating the detached target cells within the functionally closed system. In a further embodiment, the cell separation system further comprises a control module for controlling the activity in at least the cartridge and the first and second conduits. In one embodiment of any of the methods of the invention, the functionally closed system may comprises the cell separation system of any embodiment or combination of embodiments of the invention.

In another aspect, the invention provides cell suspensions, comprising
(a) a liquid medium having a volume of at least 1 mL (or, alternatively, at least 2 ml, 5 ml, 10 ml, 15 ml, 30 ml, 25 mL, at least 50 mL, at least 75 mL, at least 100 mL, at least 200 mL); and
(b) desired cells suspended in the liquid medium, wherein the desired cells are selected from the group consisting of hematopoietic stem and progenitor cells, mesenchymal stem and progenitor cells, endothelial progenitor cells found in normal blood, placental/cord blood, bone marrow, white blood cells, granulocytes, mononuclear cells, lymphocytes, monocytes, T-cells, B-cells, NK cells, the stromal vascular fraction cells resident in adipose tissue, cultured cells, genetically modified cells, and sub-populations of such desired cells, wherein the desired cells are present in a liquid medium and wherein the desired cells make up at least 80% of cells in the cell suspension;
wherein the desired cell viability is greater than 90%, or greater than 95%, or greater than 97%, or greater than 99%; and
wherein the cell suspension is present within a functionally closed cell separation system, or is directly obtained from the functionally closed cell separation system without further processing.

In one specific embodiment, the desired cells may be selected from the group consisting of CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells. In another embodiment, the functionally closed cell separation system comprises the cell separation system of any embodiment or combination of embodiments of the invention. In one embodiment, the cell suspension may be present within the transfer container, the processing container and/or the third container. In another embodiment, the cell suspension is present in a cell suspension removal stream via the transfer container of the functionally closed cell separation system.

In various embodiments, the number of viable desired cells is at least $1 \times 10^3$, or at least $1 \times 10^4$, or at least $2 \times 10^4$, or at least $5 \times 10^4$, or at least $1 \times 10^5$, or at least, $2 \times 10^5$, or at least $5 \times 10^5$, or at least $1 \times 10^6$, or at least $2 \times 10$, or at least $5 \times 10^6$, or at least $1 \times 10^7$, or at least $2 \times 10^7$, or at least $5 \times 10^7$, or at least $1 \times 10^8$, or at least $2 \times 10^8$, or at least $5 \times 10^8$, or at least $1 \times 10^9$, or at least $2 \times 10^9$, or at least $5 \times 10^9$. In another embodiment, the desired cells comprise a buoyant label attached to the cells.

In a further aspect, the invention provides compositions comprising:
(a) at least one binding agent covalently or non-covalently linked to at least one first linker, the at least one binding agent able to bind to at least one molecular target on the cells in a cell suspension; and
(b) at least one buoyant label covalently or non-covalently linked to at least one second complementary linker, the at least one buoyant label exhibiting a density substantially different from the density of the liquid medium in which the cells to be separated are suspended.

In another aspect, the invention provides kits comprising
(i) a primary binding agent comprising an agent capable of binding to at least one cellular epitope on a target cell;
(ii) a first linker bound to the agent, wherein the first linker comprises a first oligonucleotide having a first complementary region;
(iii) a buoyant label;
(iv) a second linker bound to the buoyant label, wherein the second linker comprises a second oligonucleotide having a second complementary region, wherein the second complementary region is perfectly complementarity to the first complementary region, and wherein a hybrid of the first and second complementary regions has a calculated Tm of at least 40° C.

In another aspect, the invention provides compositions comprising
(i) a primary binding agent comprising an agent capable of binding to at least one cellular epitope on a target cell;
(ii) a first linker bound to the agent, wherein the first linker comprises a first oligonucleotide having a first complementary region;
(iii) a buoyant label;
(iv) a second linker bound to the buoyant label, wherein the second linker comprises a second oligonucleotide having a second complementary region perfectly complementary to the first complementary region, wherein a hybrid of the first and second linkers' complementary regions has a calculated Tm of at least 40° C.
wherein the first linker and the second linker are hybridized to each other. In one embodiment, the composition further comprises a target cell bound to the primary binding agent.

In one embodiment of the compositions and kits of the invention, the calculated Tm may be the Tm as calculated using the nearest-neighbor two-state model:

$$Tm(^\circ C.) = \frac{\Delta H^\circ}{\Delta S^\circ + R\ln[oligo]} - 273.15$$

where $\Delta H^\circ$ (enthalpy) and $\Delta S^\circ$ (entropy) are the melting parameters calculated from the sequence and the published nearest neighbor thermodynamic parameters, R is the ideal gas constant (1.987 calK$^{-1}$ mole$^{-1}$), [oligo] is the molar concentration of an oligonucleotide, and the constant of −273.15 converts temperature from Kelvin to degrees of Celsius. In one embodiment, the calculated Tm of the hybrid between the first complementary region and the second complementary region is between 40° C. and about 60° C.

In various embodiments of the kits and compositions of the invention, the primary binding agent may be selected from the group consisting of antibodies, oligonucleotides, aptamers, molecularly imprinted polymers, carbohydrates, proteins, peptides, enzymes, small molecules, lipids, fatty acids, metal atoms, metal ions or synthetic polymers. In one specific embodiment, the primary binding agent comprises an antibody. In another specific embodiment, one of the first linker and the second linker further comprises biotin (optionally linked to a first member of an oligonucleotide hybridizing pair), and the other further comprises streptavidin (optionally linked to a second member of an oligonucleotide hybridizing pair). In various further embodiments, the buoyant labels may be selected from the group consisting of gas-filled bubbles, hollow polymers, glass beads, microporous based with entrained gas, droplets of an immiscible liquid, gold nanoparticles, and silver nanoparticles. In one specific embodiment, the buoyant labels comprise gas-filled bubbles. In various embodiments, the gas-filled bubbles may comprise perfluorocarbon gas cores encompassed by lipid, phospholipid, protein or carbohydrate shells. In a further specific embodiment, the gas-filled bubbles comprise perfluorocarbon gas cores encompassed by phospholipid shells. In another specific embodiment, the gas-filled bubbles have a diameter between about 1 um and about 6.5 um.

In another aspect, the invention provides compositions comprising desired cells purified via buoyancy-activated cell sorting from a starting admixture of at least one molecular type of desired cell and at least one molecular type of non-desired cell where said starting admixture contains at least 1 times the number of non-desired cells as desired cells, or at least 5 times the number of non-desired cells as desired cells, or at least 10 times the number of non-desired cells as desired cells, or at least 50 times the number of non-desired cells as desired cells, or at least 100 times the number of non-desired cells as desired cells, or at least 500 times the number of non-desired cells as desired cells, or at least 1000 times the number of non-desired cells as desired cells wherein:

the recovery efficiency of the at least one type of desired cell is greater than 80%, or greater than 85%, or greater than 90%, or greater than 95%;

the purity of the at least one type of desired cell is greater than 80%, or greater than 85%, or greater than 90%, or greater than 95%;

the viability of the at least one type of desired cell is greater than 90%, or greater than 95%, or greater than 97%, or greater than 99%; and the volume of the admixture of at least one molecular type of desired cell and at least one molecular type of non-desired cell subjected to buoyancy-activated cell sorting is greater than 10 mL, or greater than 50 mL, or greater than 100 mL, or greater than 150 mL, or greater than 200 mL, or greater than 400 mL, or greater than 800 mL.

BRIEF DESCRIPTION OF THE FIGURES

FIG. 11 summarizes experimental data generated using exemplary embodiments of the methods of the invention.

FIG. 12 summarizes experimental data generated using exemplary embodiments of the methods and systems of the invention.

DETAILED DESCRIPTION OF THE INVENTION

As used herein, the singular forms "a", "an" and "the" include plural referents unless the context clearly dictates otherwise. "And" as used herein is interchangeably used with "or" unless expressly stated otherwise.

As used herein, the term 'about" means +/−5% of the recited parameter.

All embodiments of any aspect of the invention can be used in combination, unless the context clearly dictates otherwise.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

The description of embodiments of the disclosure is not intended to be exhaustive or to limit the disclosure to the precise form disclosed. While the specific embodiments of, and examples for, the disclosure are described herein for illustrative purposes, various equivalent modifications are possible within the scope of the disclosure, as those skilled in the relevant art will recognize.

Figure 1:
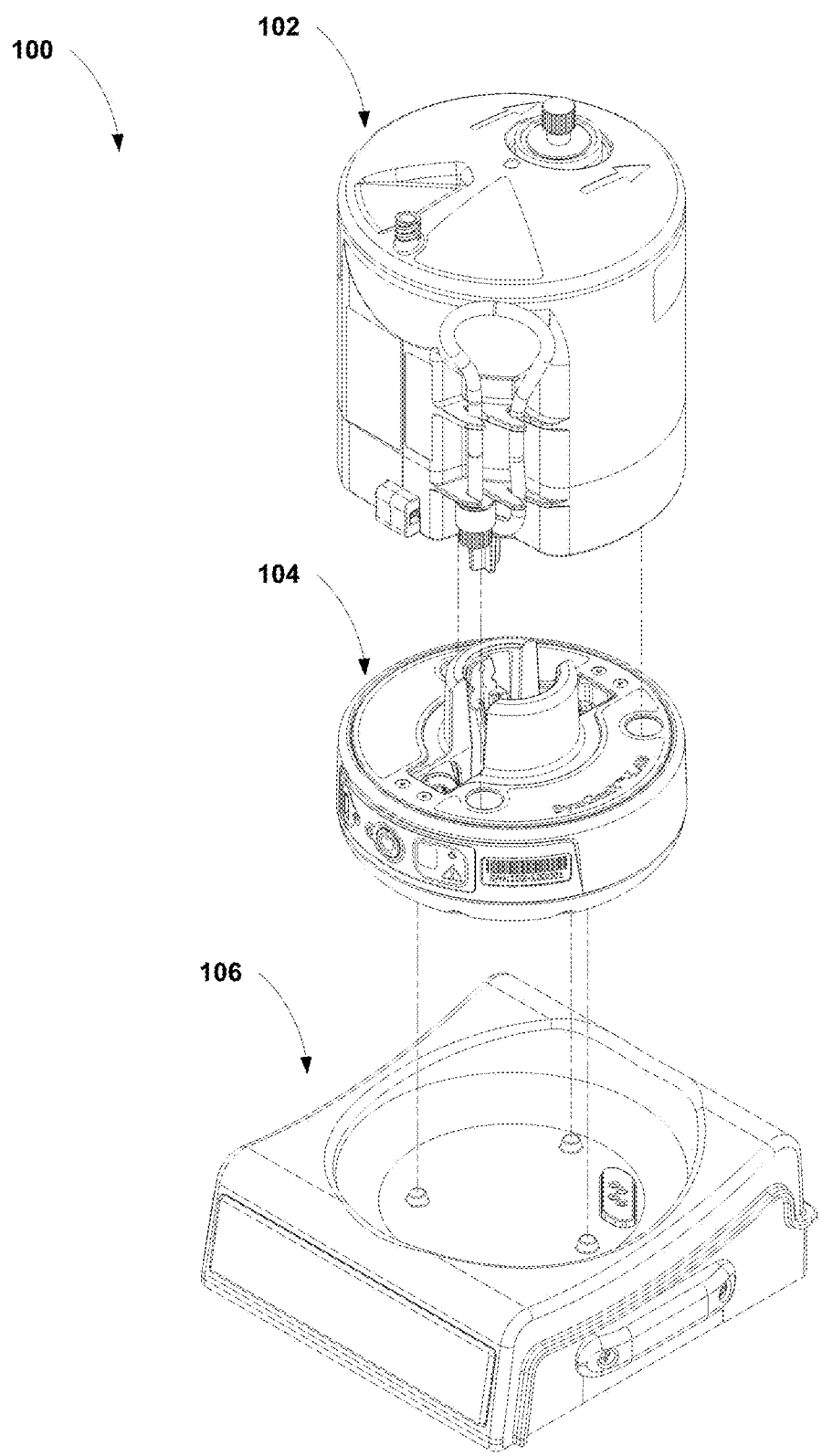
FIG. 1 is an exploded view of a cell separation system, according to an example embodiment.

With reference to the Figures, FIG. 1 illustrates an example cell separation system 100. As shown in FIG. 1, the cell separation system 100 may include a cartridge 102, a control module 104, and a docking station 106. As used herein, "cartridge" is a closed housing (having a roof) that allows the aseptic transfer of cells between containers within the closed housing and the mixing of cells, binding agents, buoyant labels, and buoyant reagents to accomplish linkage, comprising three or more mechanically joined containers which are transiently fluidically connected. The cartridge 102 may hold up to 250 mL of liquid, may be cylindrical, may be single-use, and may be constructed preferably of hard plastic, and more preferably optically clear polycarbonate. In certain other embodiments, the cartridge 102 is reusable. The control module 104 may be removably coupled to the cartridge 102. The control module 104 is an electro-mechanical device with optical and gravitational sensing. In particular, the control module 104 provides optical sensing of cell interfaces in the bottom of the cartridge 102, and may be configured to control one or more reversible closing devices to control activity between various containers of the cartridge 102, as discussed in additional detail below. The docking station 106 may be removably coupled to the control module 104, and may be used to recharge the control module 104. Further, the docking station 106 may receive one or more protocols wirelessly or through a wired connection, and may further be configured to download and process data received by the control module 104. The docking station 106 preferably uses a rechargeable battery system to power the control module 104 that monitors and controls gravitational and optical sensing equipment and directs activity in the cartridge 102. The means for determining a G force may be any commonly known in the art, such as calculating said force through a measurement of centrifuge RPM, or through direct measurement of acceleration or force.

When the cartridge 102 is removably attached to the control module 104, one or more detectors, such as optical sensors or other sensors of the control module 104 may be used to detect the type of cells flowing through the cartridge 102. Further, the control module 104 may also include at least one but preferably two or more optical or other emitters. In an exemplary embodiment, four infrared emitters/detector pairs are arranged vertically in the control module 104. In a preferred embodiment, infrared sensors are located directly across from paired infrared emitters. In second preferred embodiment, transmitters that provide wavelengths that are preferentially absorbed by red cells are located directly across from paired sensors sensitive to that frequency. In a third preferred embodiment sensors are utilized that identify cells that have absorbed fluorescent dyes. In the first preferred embodiment, the presence of cells interferes with the emitted infrared light and the infrared light detector quantifies the amplitude of the signal penetrating the fluid. In a preferred embodiment the sensors may assign the level of transmission a value from 0-1000. Pure plasma, which similar to water blocks none of the infrared light, will register a value of roughly 1000. As compacted RBCs pass between the sensor/emitter pairs, essentially all infrared light is blocked and the detector registers a value of 0.

Figure 2:
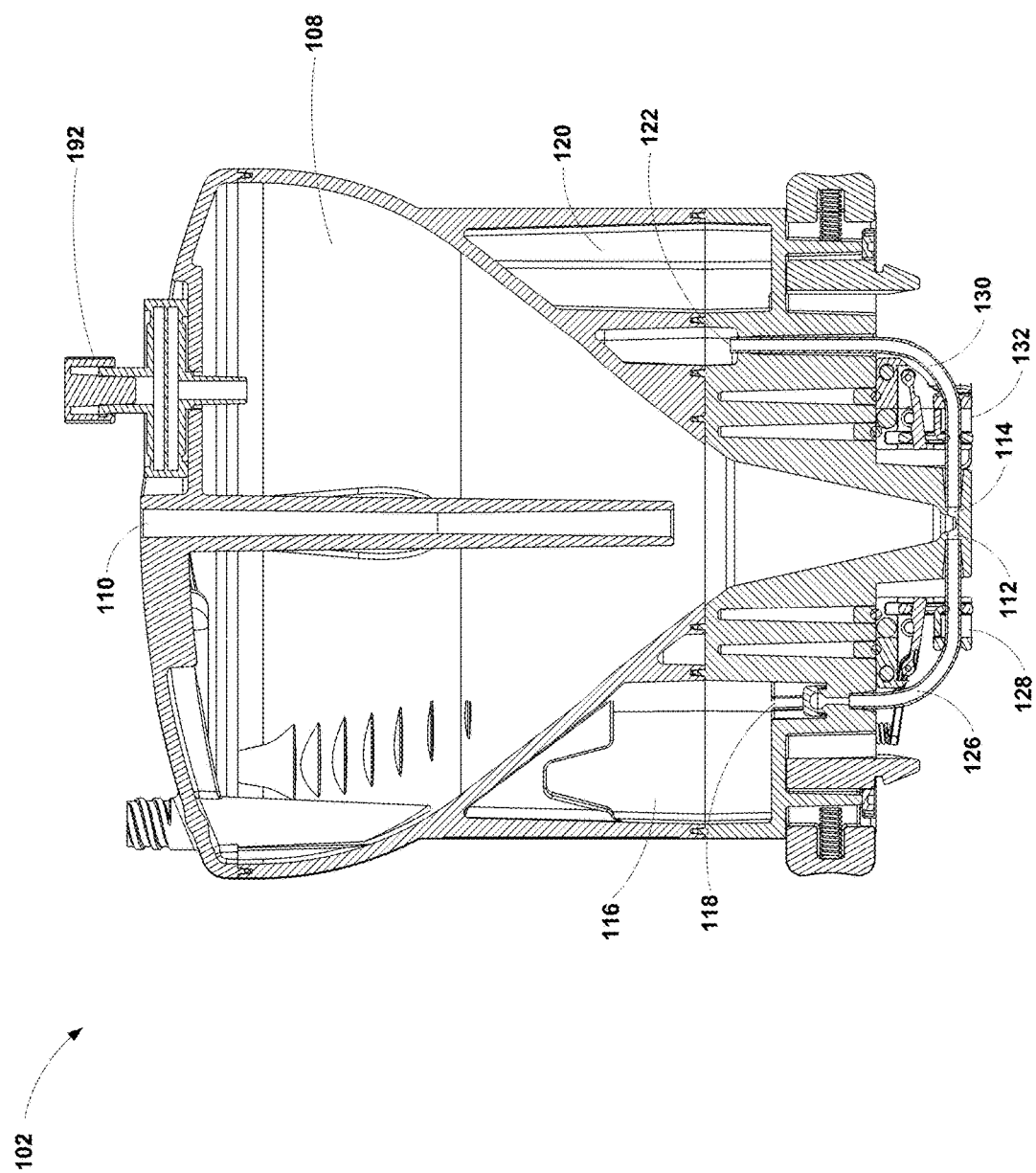
FIG. 2 is a cross-section view of a cartridge of a cell separation system, according to an example embodiment.

FIG. 2 illustrates a cross-section view of the cartridge 102. As shown in FIG. 2, the cartridge 102 includes a processing container 108 comprising at least one input port 110, a first exit port 112, and a second exit port 114. The cartridge 102 also includes a second container 116 comprising an input port 118, and a third container 120 comprising an input port 122 and a first exit port 124. As described in the process below, a biological fluid containing cells, such as normal blood, cord blood or bone marrow, is delivered to the processing container 108 through the at least one input port 110. The second container 116 of the cartridge 102 comprises a large first rigid storage compartment or RBC depletion compartment, and the third container 120 comprises a smaller second rigid storage compartment or SC compartment into which the WBCs and substantially all the SPCs are transferred. The second container 116 is significantly larger than the third container 120, as the volume of RBCs depleted from a blood sample is always much greater that the volume of WBCs collected. All compartments are distinct from one another within the cartridge 102, but contiguous with respect to airflow. The second compartment 116 and the third compartment 120 may be connected by small filtered or sufficiently narrowed air vents to the processing container 108 so as to allow displacement of air as cell solutions move from the processing chamber 108 into the second and third containers 116, 120, but does not permit fluid transfer between the containers. In one embodiment, the processing container 108 is an approximately conical central container, while the second and third containers 116, 120 are smaller, circumferentially located containers. The containers may be of any suitable volume for a given purpose. In one embodiment, the third and second containers 116, 120 each may further comprise additional, normally closed ports providing optional points of connection to any suitable receiving containers external to the cartridge 102 for gravity draining or as a result of adding air pressure through the air filter 192. In a further embodiment, fluid in the processing container 108 may be removed through the internal input tube 110 by the application of air pressure through air filter 192 with that ceases when the level of fluid in the container drops below the lowest point on the internal rigid input tube 110.

As shown in FIG. 2, the cartridge 102 also includes a first conduit 126 connecting the first exit port 112 of the processing container 108 and the input port 118 of the second container 116. The first conduit 126 comprises a first reversible closing device 128. The second container 116 is transiently fluidically connected to the processing container 108 such that fluid flow only from the processing container 108 to the second container 116 may occur when the first reversible closing device 128 is opened. The cartridge 102 also includes a second conduit 130 connecting the second exit port 114 of the processing container 108 and the input port 122 of the third container 120. The second conduit 130 comprises a second reversible closing device 132. The third container 120 is transiently fluidically connected to the processing container 108 such that fluid flow only from the processing container 108 to the third container 120 may occur when the second reversible closing device 132 is opened.

As used herein, a "reversible closing device" is any device that can be closed (such as a by a controller) to prohibit fluid flow. Exemplary such devices include, but are not limited to valves, clamps, and stopcock. As used herein, "transiently fluidically connected" means that the containers are fluidically non-continuous (that is, each functionally closed) other than when transiently connected via opening of the device's normally closed valves to achieve aseptic transfer of fluid or cell suspension from one container to another. The "conduits" may be any suitable device to permit fluid transfer between the containers, including but not limited to tubing. All of the conduits become "normally closed", such that the containers are not fluidically connected, as soon as the operator removes a pin installed during cartridge assembly that prevents the conduits from being closed. The conduits may be closed by any suitable reversible closing device, such as a valve, clamp or stopcock. In one embodiment, the conduits within the cartridge may be closed by a spring loaded, tube pinching mechanism at all times except when fluids should pass, at which time the pinching mechanism may be rotated (for example, by a control module automatically controlling the reversible opening of the conduit) to allow passage of the fluids, and then may be rotated again to allow the spring loaded tube pinching mechanism to close off that passage by re-pinching the conduit. In such an example, the reversible closing devices comprise two opposing clamps having pinching surfaces approximately 0.088 inches wide, and require approximately 1.6 pounds of pinching force to block all fluid passage through a urethane tube with an inner diameter of 0.062 inches and an exterior diameter of 0.088 inches when the hydraulic pressure in the tube is at 325 PSI. Pinching forces in excess of 1.6 pounds may be required at greater pressures, and reduced pinching forces may be sufficient at lower pressures. In such an example, a cantilever system may be used to achieve these required pinching pressures. The cantilever system may open and close the conduits (pinch and release the tubing) as needed. Springs may be provided on each cantilever, and are preferably located at the extreme end of the cantilever. The actuator overcomes the resistance of the springs to move the lever. Once the actuator stops applying force, the bias of the springs urges the lever back to its first position.

As described above, the processing container 108, or other containers may optionally be interrogated by at least one detector for detecting the presence or absence of cells. In such an embodiment, the control module 104 controls opening and closing of the first reversible closing device 128 and/or the second reversible closing device 132 based on information relayed from the at least one detector. Any suitable detector may be used, including but not limited to optical detectors, as discussed above in relation to FIG. 1.

As will be described in detail below, in operation, the RBCs initially migrate towards the bottom of the processing container 108, moving radially outward away from the axis of rotation of the centrifuge until reaching the bottom of the processing container 108, where the first reversible closing device 128 and the second reversible closing device 132 reside. Here, the pressure head of fluid above the bottom of the processing container 108 urges the fluid into one of two compartments: either the second container 116 or the third container 120. Which compartment the fluid is directed into is dependent upon the status (open, closed) of the first reversible closing device 128 and the second reversible closing device 132. In either case, after passing through the first reversible closing device 128 and/or the second reversible closing device 132, the fluid flows generally toward the axis of rotation, urged by pressure from the of fluid (mostly plasma) remaining in the processing container 108. The fluid that has passed through the first reversible closing device 128 and/or the second reversible closing device 132 is then retained in either the second container 116 or the third container 120. Through minute adjustments of the first reversible closing device 128 and/or the second reversible closing device 132, unwanted cell solutions may be depleted and desired cell solutions may be harvested.

Figure 3:
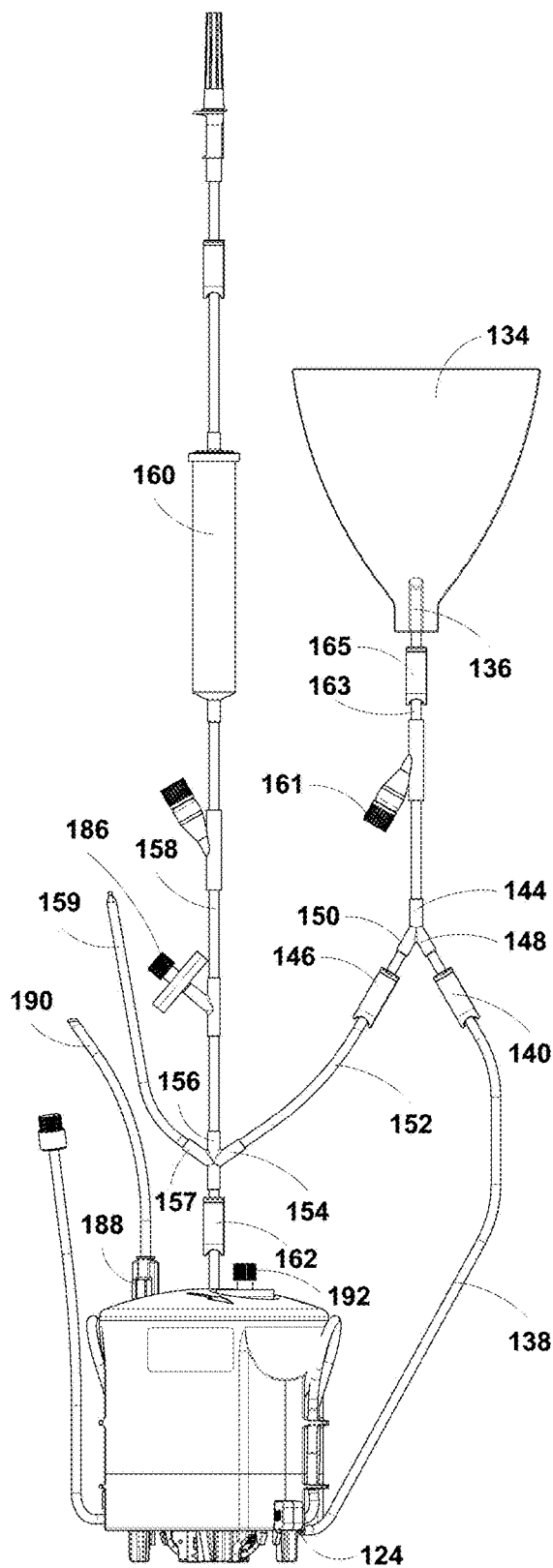
FIG. 3 is a side view of a cell separation system, according to an example embodiment.

As shown in FIG. 3, the cell separation system 100 may further include a transfer container 134 comprising at least one port 136. The transfer container 134 may be mechanically coupled to the cartridge 102, or may be physically connected only via the relevant conduit connecting the transfer container 134 to containers within the cartridge 102 to maintain the system as a functionally closed system. As such, in one embodiment, the transfer container 134 is internal to the cartridge 102; in another embodiment the transfer container 134 is external to the cartridge 102. The various containers may comprise any suitable material, such as a rigid structure, a bag, a bottle, or any other suitable structure. In one embodiment, each container is a rigid container, such as a hard plastic container (including but not limited to polycarbonate). In another embodiment, the transfer container 134 is a flexible container, including but not limited to a bag. The transfer container 134 can be a rigid container, because the air in the container at the start of the transfer of harvested target cells in solution can displace along the relevant conduit connecting it to the processing container. The transfer container 134 also can be a flexible container, which has the advantage of being foldable into a small shape to make it easier to store, for example, in the rotor compartment of a centrifuge during centrifugation.

Further, as shown in FIG. 3, the cell separation system 100 further includes an at least third conduit 138 connecting the first exit port 124 of the third container 120 to the at least one port 136 of the transfer container 134, and the at least one port 136 of the transfer container 134 to the at least one input port 110 of the processing container 108. The at least third conduit 138 comprises at least a third reversible closing device 140, such that the third container 120 is transiently fluidically connected to the transfer container 134, and the transfer container 134 is transiently fluidically connected to the processing container 108. The at least third conduit 138 is configured such that only one of the following may be true: (I) fluid flow only from the third container 120 to the transfer container 134 may occur when the at least third reversible closing device 140 is opened, or (II) fluid flow only from the transfer container 134 to the processing container 108 may occur when the at least third reversible closing device 140 is opened.

The third conduit 138 between the first exit port 124 of the third container 120 to the transfer container 134 and from the transfer container 134 to the at least one input 110 of the processing container 108 is also normally closed by any suitable reversible closing device. In one embodiment, the third conduit 138 may be clamped on the exterior of the cartridge 102 by the third reversible closing device 140 (just adjacent to the first exit port 124 of the third container 120) and may be unclamped at the time of transfer of sequestered attached cells from the third container 120 to the transfer container 134 (for example, by gravity draining the sequestered attached cells from the third container 120 to the transfer container 134). Following transfer into the transfer container 134, the third reversible closing device 140 on the third conduit 138 adjacent to the third container port 124 may be re-clamped. At that time, for example, the sequestered attached cells may be transferred to the processing container 108 via the third conduit 138 (for example, by gravity draining the sequestered attached cells back into the processing chamber 108, for further processing—such as isolating/enriching a sub-population of the sequestered, attached cells, including but not limited to mononuclear cells to join the cell-free and platelet free plasma from the host liquid). The transfer container 134 therefore provides an economic advantage as the cartridge 102 may be reused. Additionally, the transfer container 134 allows for improved mixing the target cell suspension and BAGS reagents.

The cell separation system 100 may further include a control module 104, as discussed above in relation to FIG. 1. The control module 104 may be configured to control activity in at least the cartridge 102, and the first and second conduits 126, 130. In some embodiments, the control module 104 may also control activity within the transfer container 134 and/or within the third conduit 138. For example, the control module 104 may control activity within the transfer container 134 and/or within the third conduit 138 in embodiments in which the transfer container 134 is present within the cartridge 102. The control module 104 may control the reversible closing devices 128, 132, 140 that direct the flow of fluid between the cartridge containers 108, 116, 120, such as when placed in a centrifuge. In one non-limiting embodiment, the cartridge 102 containing the target cell/buoyant label mixture is centrifuged so that target cells that bind to the buoyant label separate from the cells not bound to the buoyant label. The control module 104 may be programmed to deliver the non-buoyant pelleted cells to the second container 116 of the cartridge 102 via the first reversible closing device 128, leaving the bulk of the supernatant and substantially all of the target cells that bound to the buoyant reagent in the processing container 108 of the cartridge 102.

In one embodiment, the at least third conduit 138 comprises a single conduit. In this embodiment, the only a single conduit is fluidically coupled to the transfer container 134, and the conduit can be fluidically separated such that fluid flowing from the third container 120 to the transfer container 134 is separated from fluid flowing from the transfer container 134 to the processing container 108. Any suitable reversible closing means can be used in this embodiment. One non-limiting example is shown in FIG. 3, in which the at least third conduit 138 comprises a T or Y connector 144 disposed between the third container 120 and transfer container 134, and between the transfer container 134 and the processing container 108, with appropriate reversible closing devices 140, 146 to regulate the desired fluid flow.

In a further embodiment, the at least one port of the transfer container comprises a first input port 148 and an exit port 150. In this embodiment, the at least third conduit 138 may comprise (i) a third conduit 138 connecting the exit port 124 of the third container 120 to the input port 136 of the transfer container 134, wherein the third conduit 138 comprises a third reversible closing device 140, such that the third container 120 is transiently fluidically connected to the transfer container 134 such that fluid flow only from the third container 120 to the transfer container 134 may occur when the third reversible closing device 140 is opened, and (ii) a fourth conduit 152 connecting the exit port 136 of the transfer container 134 to the at least one input port 110 of the processing container 108, wherein the fourth conduit 152 comprises a fourth reversible closing device 146, such that the transfer container 134 is transiently fluidically connected to the processing container 108, such that fluid flow only from the transfer container 134 to the processing container 108 may occur when the fourth reversible closing device 146 is opened. In this embodiment, separation of fluid flowing from the third container 120 to the transfer container 134 away from fluid flowing from the transfer container 134 to the processing container 108 is made possible by the use of completely separate conduits 138, 152.

In a still further embodiment, the at least one input port 110 of the processing container 108 comprises a first input port 154 and a second input port 156, wherein the at least third conduit 138, or the fourth conduit 152 (when present), connects the exit port 136 of the transfer container 134 to the first input port 154 of the processing container 108. In such an example, the cell separation system 100 may further comprise a first medium input conduit 158 connecting the second input port 156 of the processing container 108 to at least one medium reservoir 160, wherein the first medium input conduit 158 comprises at least a fifth reversible closing device 162, wherein the at least one medium reservoir 160 is transiently fluidically connected to the processing container 108 such that fluid flow only from the at least one medium reservoir 160 to the processing container 108 may occur when the at least fifth reversible closing device 162 is opened.

The medium input reservoir(s) 160 can be used to supply host liquid, binding agents, buoyant labels, and/or buoyant reagents to the processing container 108 via the second input port 156.

In yet another embodiment, the at least one input port 110 of the processing container 108 comprises a third input port 157. The third input port 157 may be coupled to a fifth conduit 159. In such an example, liquid can be removed from the processing chamber 108 by providing positive pressure at the filter 186.

In one embodiment, the at least one port of the transfer container 134 further comprises a second input port 161. For example, the cell separation system 100 may further comprise a second medium input conduit 163 connecting the second input port 161 of the transfer container 134 to at least one medium reservoir (not shown), wherein the second medium input conduit 163 comprises at least a sixth reversible closing device 165, wherein the at least one medium reservoir is transiently fluidically connected to the processing container 108 such that fluid flow only from the at least one medium reservoir to the transfer container 134 may occur when the at least sixth reversible closing device 165 is opened.

The media input reservoir(s) can be used to supply host liquid, binding agents, buoyant labels, and/or buoyant reagents to the transfer container 134 via the second input port 161. In embodiments where at least one medium reservoir is transiently fluidically connected to both the processing container 108 and the transfer container 134, the media reservoir(s) may be the same reservoirs, or each container may have its own dedicated reservoir(s).

In a further embodiment, the cell separation system 100 further comprises a mixer. The mixer may be used, for example, to promote/improve mixing of (a) the buoyant reagents and the host liquid, and/or (b) the buoyant labels, binding agents, and linkers (when present), and/or (c) buoyant labels, binding agents, linkers (when present), and host liquid. In one embodiment, the mixer is a static mixer. A static mixer comprises container with an input and exit that remains stationary while providing continuous mixing of two fluids simultaneously passing through the container, in a configuration such as, but not limited to, a cylindrical tube containing mixer elements oriented throughout the interior length of the cylindrical tube.

Figure 4B:
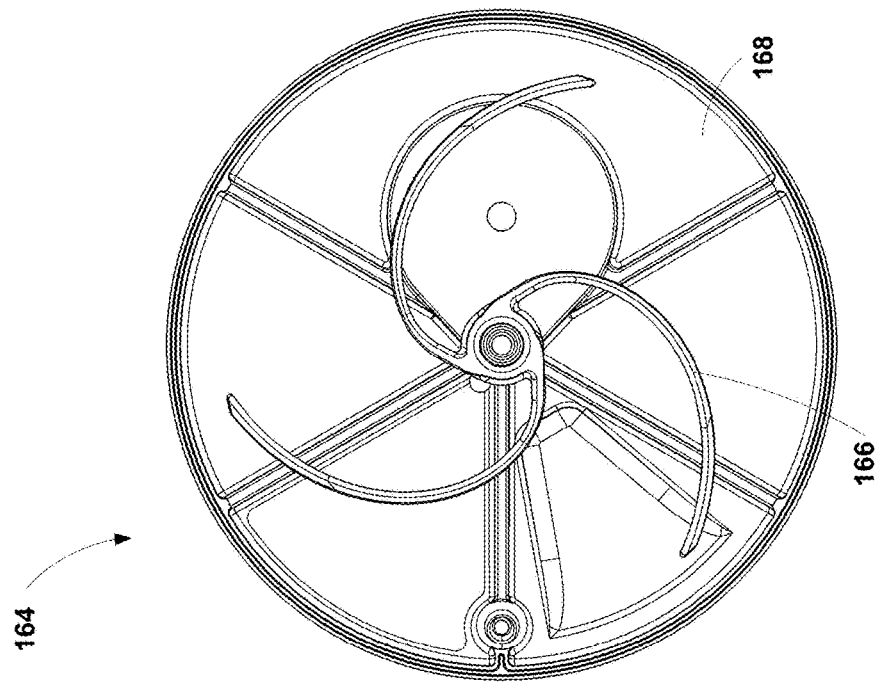
FIG. 4B is a bottom view of the example static mixer of FIG. 4A, according to an example embodiment.
Figure 4A:
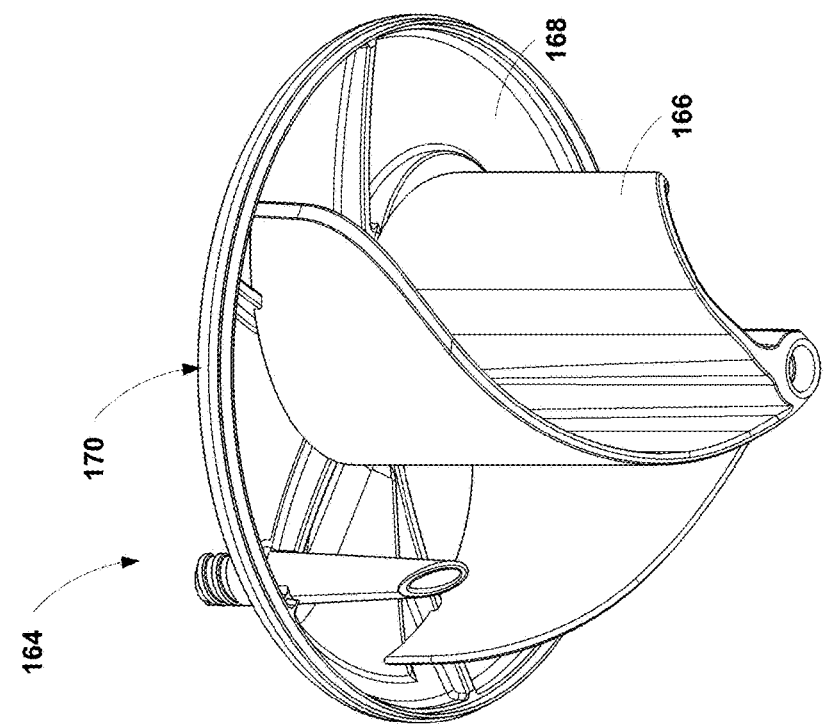
FIG. 4A is a perspective view of an example static mixer on the roof of the cartridge, according to an example embodiment.

Exemplary static mixers appropriate for mixing in the devices of the invention (such as mixing a target cell suspension (major component) and BACS reagents (additive)) are shown in FIGS. 4A-5B. The medium reservoirs described above may be transiently fluidically connected to the static mixer via the fifth and sixth reversible closing devices. In one non-limiting embodiment, as shown in FIGS. 4A and 4B, the static mixer 164 acts to rotate the cartridge 102 on its axis by including an impeller 166 affixed to the internal surface 168 of the cartridge roof 170 causing, for example, a BACS reagent and target cells in solution within the processing container to admix. The advantage of the design in FIGS. 4A-4B is that the mixing addition to the interior of the cartridge is glued in place, so mixing of the in cell solution and the BACS reagents occurs merely by placing the loaded cartridge on a roller table device for a programmable time.

Figure 5B:
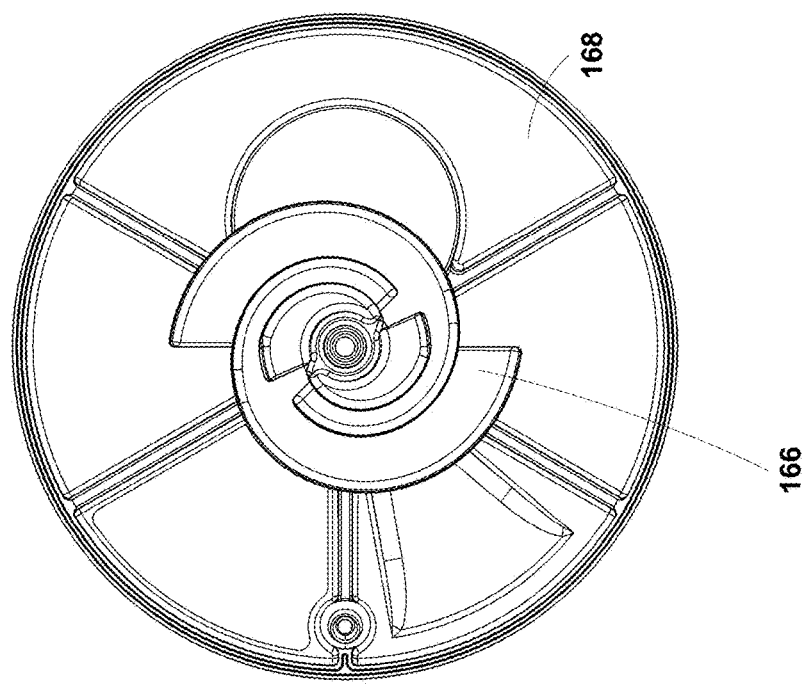
FIG. 5B is a bottom view of the example static mixer of FIG. 5A, according to an example embodiment.
Figure 5A:
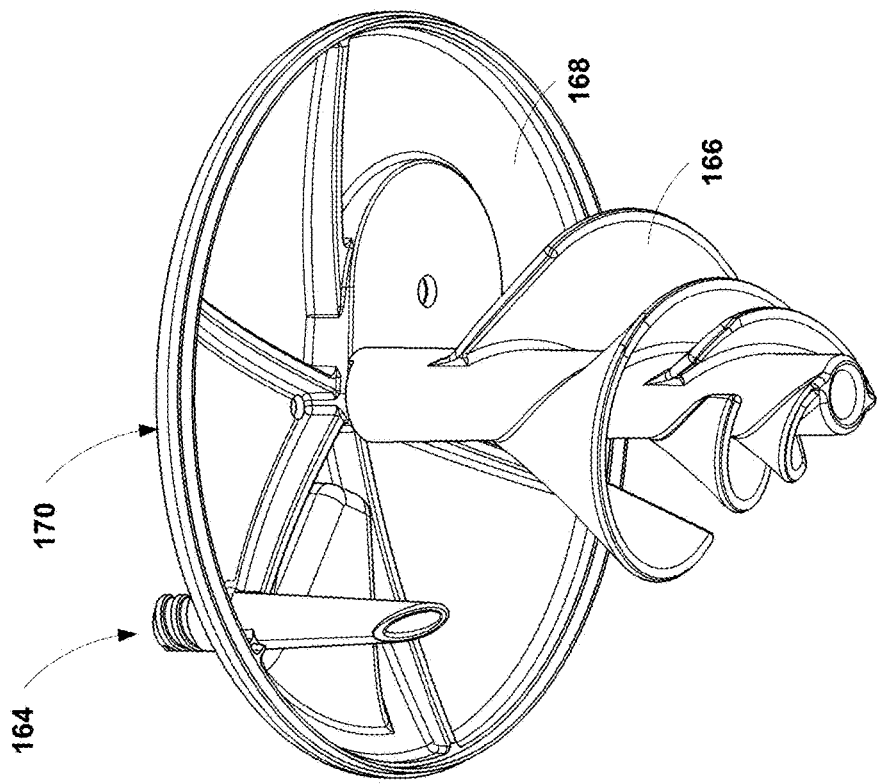
FIG. 5A is a perspective view of another example static mixer on the roof of the cartridge, according to an example embodiment.

In another non-limiting embodiment, as shown in FIGS. 5A and 5B, the static mixer 164 acts to rotate the cartridge 102 on its axis by including an impeller 166 spaced away from the internal surface 168 of the cartridge roof 170 causing, for example, a BACS reagent and target cells in solution within the processing container to admix. The advantage of the design in FIGS. 5A-5B is that the mixing addition to the interior of the cartridge rotates on its axis, driven by a motor means, so that the cartridge remains upright and does not have to be removed from the centrifuge.

Figure 6:
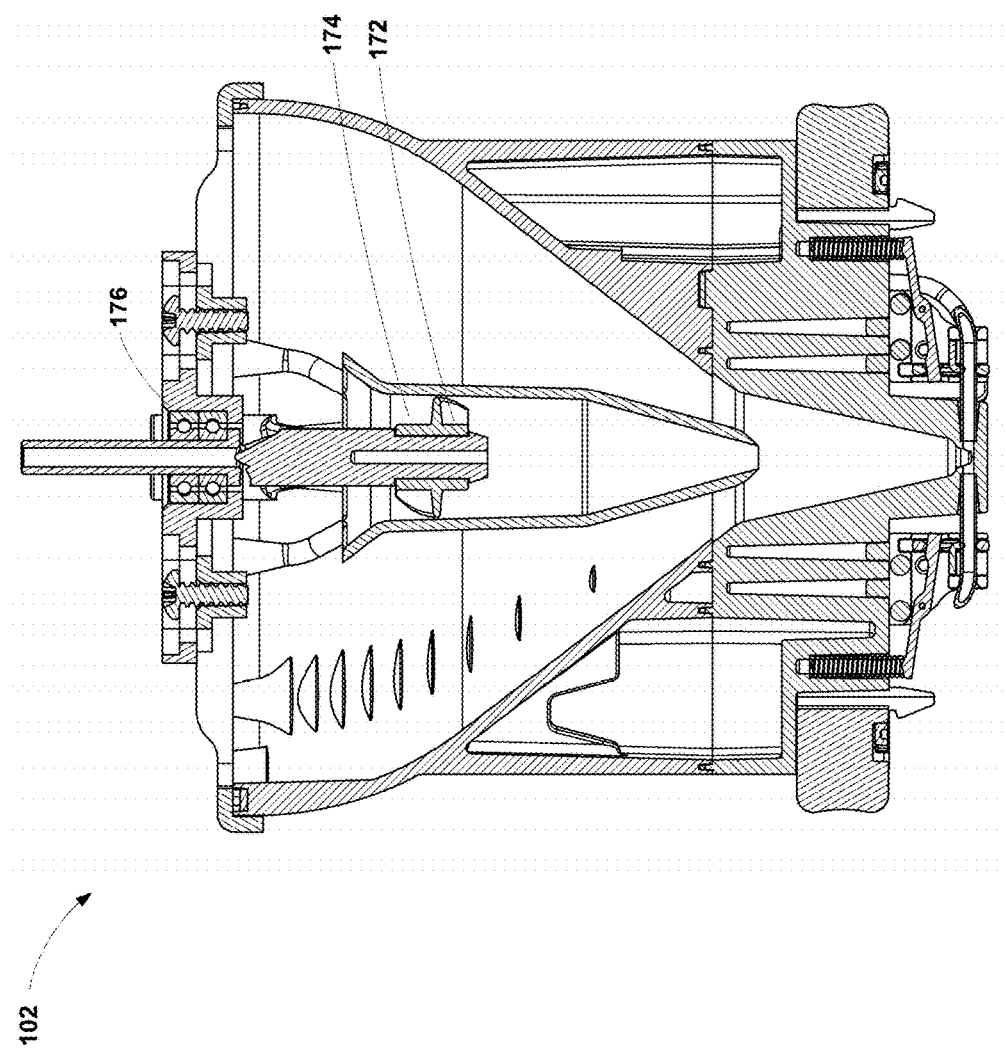
FIG. 6 is a cross-section view of an example mixer in the funnel of the cartridge, according to an example embodiment.

In another non-limiting embodiment, as shown in FIG. 6, the mixer acts to impart circulating motion to an admixture of BACS reagent and target cells in solution within the processing container 108 of the cartridge 102 while the cartridge 102 remains motionless. Such an embodiment may include an impeller 172 positioned within a cylindrical tube 174, with a motor 176 configured to drive the impeller 172 to thereby cause the mixing in the processing container 108.

Figure 7:
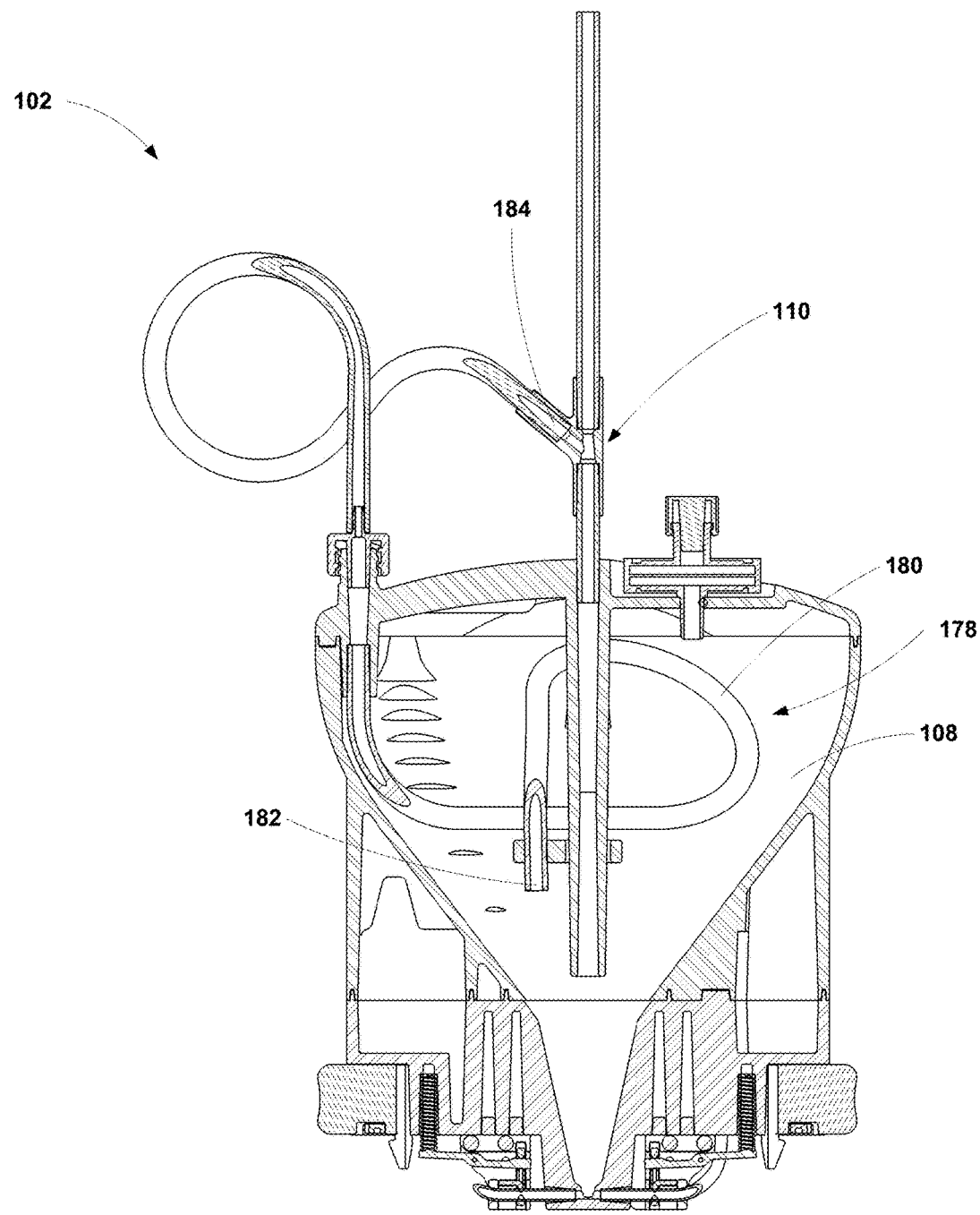
FIG. 7 is a cross-section view of an example peristaltic pump of the cartridge, according to an example embodiment.

In another non-limiting embodiment, as shown in FIG. 7, the mixer comprises a peristaltic pump 178 comprising a pump conduit 180 having a first end 182 and a second end 184, wherein the first end 182 of the pump conduit 180 is positioned in the processing chamber 108, and wherein the second end 184 of the pump conduit 180 is positioned outside of the processing chamber 108 and is connected to the at least one input port 110 of the processing chamber 108.

Figure 8:
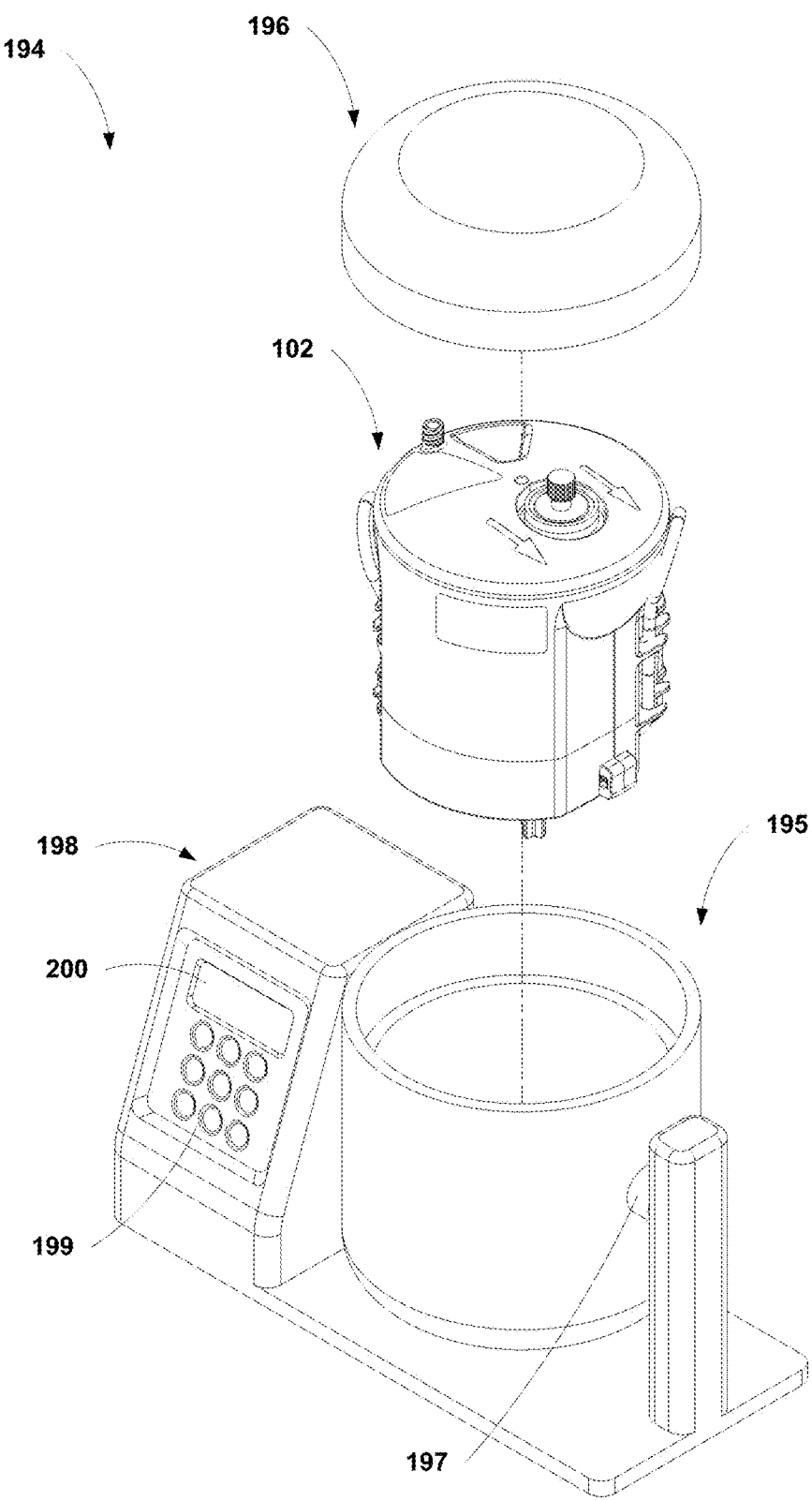
FIG. 8 is an exploded view of an example mixing module, according to an example embodiment.

In yet another non-limiting embodiment, as shown in FIG. 8, the mixer comprises a mixing module 194. The mixing module may include a bottom portion 195 and a top portion 196. As shown in FIG. 8, the cartridge 102 may be configured to be positioned in the bottom portion 195, and the top portion 196 may be configured to be removably coupled to the bottom portion 195. As such, the cartridge 102 may be positioned in a chamber created by the bottom portion 195 and the top portion 196. In one non-limiting embodiment, the mixing module 194 may include a rotatable component 197 coupled to the bottom portion 195. The rotatable component 197 may be configured to rotate the cartridge 102 on its vertical axis. The rotatable component 197 may be coupled to a motor, which in turn causes the bottom portion 195 of the mixing module 194 to rotate. In one particular example, the rotatable component 197 is configured to rotate the cartridge 102 on its vertical axis by 180 degrees, so the bottom of the cartridge 102 is in a vertical position, and then the rotatable component 197 causes the cartridge 102 to rotate back 180 degrees to an original upright position. In another example, the rotatable component 197 is configured to rotate the cartridge 102 end over end continuously over 360 degrees at various rotational rates for a period of time. In another non-limiting embodiment, the bottom portion 195 of the mixing module 194 may be configured to vibrate to assist in mixing. In another non-limiting embodiment, the mixing module 194 may be configured to increase a temperature of the cartridge 102 when the cartridge is positioned 102 in the bottom portion 195 of the mixing module 194. Such an increase in temperature may occur through conduction, convection, or radiation heating in the bottom portion 195 of the mixing module 194.

As shown in FIG. 8, the mixing module 194 may include a mixing control module 198, which may include a control panel 199 and a display 200. The control panel 199 may be used to select a time period for mixing, as well as one or more mixing parameters. For example, a user could select 180 degree mixing for a period of time, 360 degree mixing for a period of time, heating at a specific temperature for a period of time, and/or vibrating for a period of time. Other examples are possible as well.

In various embodiments, the first medium input conduit 158 and/or the second medium input conduit further comprise a filter 186. Any suitable filter (including but not limited to a 0.2 micron filter, or other appropriately sized filter to remove large particles) can be used in connection with the medium input conduit(s) to promote aseptic introduction of medium into processing container and/or target container. Exemplary placement of such filters can be seen, for example, in FIG. 3.

In another embodiment, the second container 116 comprises an exit port 188 coupled to a first waste conduit 190. This embodiment permits removal of waste product from the second container 116. In a further embodiment, the processing container 108 further comprises a sterile vent 192 coupled to a second waste conduit (not shown). This embodiment permits removal of waste product from the processing container 108. Exemplary placement of such a sterile vent 192 can be seen, for example, in FIGS. 1 and 2.

In another aspect, the invention provides methods for cell separation, comprising:

(a) processing a host liquid having a volume of at least 10 mL (or, alternatively, at least 25 mL, at least 50 mL, at least 75 mL, at least 100 mL, at least 200 mL, etc.) in a functionally closed system, wherein the host liquid comprises (i) target cells, and (ii) buoyant reagents, wherein the processing comprises contacting the target cells and buoyant reagents for a time and under conditions suitable to promote attachment of the cells to one or more of the buoyant reagents to generate attached target cells, (b) applying a vectorial force, such as centrifugation, to the host liquid within the functionally closed system to cause the attached target cells to stratify within the host liquid; and (c) sequestering the attached target cells to an area within the functionally closed system.

All steps in the methods of this aspect of the invention are carried out in the functionally closed system to maintain sterility and to permit the processing of much larger volumes of host liquid for isolation of desired cells with greater efficiency and viability, and at higher concentration than was possible using previous cell separation methods. All fluid transfer and processing steps occur under aseptic conditions and the environment remains closed and sterile.

As used herein, a "functionally closed system" is a container or collection of containers which remain(s) internally aseptic while permitting intermittent fluid transfers between aseptic containers and/or gas exchange with its surrounding atmosphere.

As summarized in Table 1 below, processing of cord blood and peripheral blood (exemplary host liquids) enables depletion of red blood cells (RBCs) by 99.6%, granulocytes by 80% and platelets by 84%, to produce mononuclear cells (MNC) enriched fractions (referred to in the table as "BACS MNC prep," to the left of the bold vertical line running through the table). Following this initial MNC enrichment, RBCs and platelets still predominate, such that MNCs still represent only a small fraction of the enriched cell population, and specific cells expressing an extracellular molecular target, such as CD34+ and CD3+ cells represent only a very low percentage of the enriched MNC cell preparation. The present invention provides a dramatic increase in the ability to isolate target cells harboring a molecular marker of interest, by further depleting RBC to a final depletion of 99.999%, granulocytes 99.9999% (cord blood) or 99.96% (peripheral blood) and platelets 98.2% (referred to in the table as "BACS final" and 'BACS cell selection efficiency", to the right of the bold vertical line running through the table). The methods of the invention enable depletion of non-target MNCs to 99.993% (cord blood) or 98.788% (peripheral blood) whilst recovering target cells with a selection efficiency of 79% (cord blood) or 80% (peripheral blood). The methods of the invention thus provide an exponential increase in the ability to isolate target cells of interest in a cell population from volumes of starting host liquid that are necessary for clinical applications. The present invention's combination of very high retention of target cells in the preliminary MNC preparation step and high recovery of target cells in the BACS cell isolation step, resulting in high overall efficiency, illustrates the commercial and therapeutic benefits of the present invention in the frequently encountered situations where either cell manufacturing costs or therapeutic outcomes are optimized by using as many target cells as possible.

TABLE 1

|  | Cord blood: Cells per 100 CD34+ cells | BACS MNC prep: recovery (+%) or depletion (-%) | BACS MNC prep: cells per 100 CD34+ starting cells | BACS final: recovery (+%) or depletion (-%) | BACS final: cells per 100 CD34+ starting cells | BACS cell selection efficiency: (%) |
|---|---|---|---|---|---|---|
| CD34+ | 100$^*$ | +99 | 99$^*$ | +80 | 79$^*$ | +79 |
| MNCs | 27,778$^*$ | +94 | 26,250$^*$ | -99.992 | 2 | -99.993 |
| GRNs | 69,445 | -80 | 13,681 | -99.999 | 0.1 | -99.9999 |
| PLTs | 2,916,690 | -89 | 352,919 | -94.3 | 2 | -99.9999 |
| RBCs | 97,223,000 | -99.6 | 388,892 | -99.999 | ND | ND |

|  | Peripheral blood: Cells per 100 CD3+ cells | BACS MNC prep: recovery (+%) or depletion (-%) | BACS MNC prep: cells per 100 CD3+ starting cells | BACS final: recovery (+%) or depletion (-%) | BACS final: cells per 100 CD3+ starting cells | BACS cell selection efficiency: (%) |
|---|---|---|---|---|---|---|
| CD3+ | 100$^*$ | +94 | 94$^*$ | +85 | 80$^*$ | +80 |
| MNCs | 165$^*$ | +94 | 155$^*$ | -98.7 | 2 | -99.788 |
| GRNs | 250 | -80 | 50 | -99.8 | 0.1 | -99.96 |
| PLTs | 1,000 | -89 | 110 | -98.2 | 2 | -99.8 |
| RBCs | 3,500,000 | -99.6 | 14,000 | -99.999 | ND | ND |

As shown in the examples that follow, the methods of the present invention provide satisfactory target cell recovery efficiencies (greater than 70%) at cell densities ranging from just $5 \times 10^6$ cells per mL to at least $105 \times 10^6$ cells per mL—more than a 20-fold range, and the latter a suspension in which cells comprise roughly 20% of the total volume. This robust and consistent performance over such a wide cell density range, including at very high cell densities, is a surprising result because the buoyant labels themselves are large particles (um-scale nominal diameters, such as gas-filled bubbles)) with accordingly limited ability to translate through dense suspensions, unlike much smaller reagents such as magnetic nanoparticles (nominal diameter 50 nm). In order to achieve high recovery efficiencies every cell likely needs to bind to multiple buoyant reagents. This, combined with the likelihood that not every cell/bubble collision will result in a productive binding event, renders it surprising that relatively large buoyant reagents can be mixed with a very dense cell suspension sufficiently well to achieve satisfactory target cell recoveries in reasonable times, without the application of shear forces that would unacceptably compromise cell viability.

As used herein, a "host liquid" is a raw source of desired cells (including but not limited to whole blood, placental/cord blood, bone marrow, leukapheresis, buffy coat, a suspension of cultured cells, or of genetically modified cells, or of other manufactured cells, etc.), admixed with non-desired cells, which may be diluted or undiluted (for example, diluted with buffers or any other liquid useful in isolating desired cells, such as saline, phosphate buffered saline, a cell culture medium, a protease solution, etc.). In one embodiment, the host liquid is peripheral blood, cord blood, or leukapheresis, or diluted versions thereof.

In one embodiment, the host liquid may be a "non-depleted" host liquid, in that all cells normally present in the relevant host liquid remain present. In another embodiment, the host liquid may comprise a depleted host liquid. A "depleted" host liquid is a host liquid from which a substantial fraction (for example, at least 50%; in other embodiments, at least 60%, 70%, 75%, 80%, 85%, 90%, 91%, 92%, 93%, 94%, 95%, 96%, 97%, 98%, 99%, or more) of one or more types of non-desired cells have been depleted. By way of non-limiting examples, a depleted host liquid may comprise desired cells in suspension after depletion of red blood cells from whole blood via density centrifugation, differential centrifugation, or lysis, or from which red blood cells and granulocytes have been depleted, or from which platelets have been depleted, or may comprise a suspension of genetically modified cells from which non-modified cells have been depleted, or may comprise a digested tissue sample from which non-stem cells have been depleted, or may comprise a digested tumor sample from which non-neoplastic cells have been depleted. In all embodiments of depleted host liquid, the desired cells may be suspended in any suitable liquid, including but not limited to saline, phosphate buffered saline, a cell culture medium, diluted or undiluted original host liquid (i.e.: whole blood, etc.).

As used herein, a "desired cell" (plural, "desired cells") is the cell or cells to be enriched or isolated in an intermediate output or the final output of the methods of this invention.

As used herein, a "target cell" (plural, "target cells") is a cell or cells to which buoyant reagents are attached in order to separate them from other cells by the methods of the present invention. In one embodiment, the target cells are the desired cells (i.e.: positive selection). In another embodiment, the target cells make up all or a portion of the non-desired cells (i.e.: negative selection). The methods and systems of the invention may be used with any suitable target cell. In various non-limiting embodiments, the target cells may be selected from the group consisting of tumor cells, cancer stem cells, hematopoietic stem and progenitor cells, mesenchymal stem and progenitor cells, adipose-derived stem and progenitor cells, endothelial progenitor cells found in normal blood, placental/cord blood, bone marrow, white blood cells, granulocytes, mononuclear cells, lymphocytes, monocytes, T-cells, B-cells, NK cells, the stromal vascular fraction cells resident in adipose tissue, cultured cells, genetically modified cells, and sub-populations of such target cells. In various specific embodiments, the target cells may be of CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells.

In one embodiment, the host liquid comprises a dilution of an initial cell suspension of desired cells. In this embodiment, the host liquid immediately before processing by the methods of this invention may be diluted up to 50×, to 40×, 30×, 20×, 10×, 4× (i.e.: 4-fold), up to 3×, up to 2×, up to 1×, up to 0.5×, up to 0.25×, up to 0.1×, or less as appropriate for a given cell separation procedure. Any suitable diluent may be used. In one non-limiting embodiment, the desired cells are CD3+ cells, and the host liquid may comprise a dilution of between 2×-4× of the initial undiluted host liquid.

As used herein a "buoyant label" is a material that (upon cell attachment) results in a complex of cell and buoyant labels with a density substantially different from the density of target cell alone and/or the density of the host liquid. Suitable such buoyant labels may include, without limitation, gas-encapsulating bubbles with protein or lipid shells, hollow polymers, glass beads (either hollow or solid), microporous beads with entrained gas, droplets of an immiscible liquid, gold nanoparticles, and silver nanoparticles. In one specific embodiment, the buoyant labels comprise gas-encapsulating bubbles, such as those encompassed by protein, lipid, phospholipid, or carbohydrate shells. In one embodiment, the gas-filled bubbles comprise perfluorocarbon gas cores encompassed by a phospholipid shell. In any of these embodiments, the gas-filled bubbles may have any suitable diameter; in one non-limiting embodiment, the gas-filled bubbles have a diameter between about 1 um and about 6.5 um.

In one embodiment, the buoyant label comprises at least one binding agent attached to it, either covalently or non-covalently; the attachment may optionally be via a linker. This embodiment is referred to herein as a "buoyant reagent". As used herein, a "binding agent" is a structure, such as a molecule, that is capable of binding with sufficiently high affinity and specificity to at least one cellular epitope on at least one target cell. Suitable binding agents may include, without limitation, antibodies, oligonucleotides, aptamers, molecularly imprinted polymers, carbohydrates, proteins, peptides, enzymes, small molecules, lipids, fatty acids, metal atoms, metal ions and synthetic polymers. In one embodiment, the binding agent comprises an antibody that selectively binds to a cellular epitope on the target cell. As used herein, a "primary binding agent" is a binding agent that has no buoyant label attached to it. As used herein, a "linker" (or, individually "a linker") comprises a pair of chemical moieties (a first linker and a second linker) attached covalently or non-covalently one to a binding agent the other to a buoyant label, which are able to spontaneously attach (either covalently or non-covalently) to each other in a suitable medium under suitable conditions with sufficiently high affinity to achieve the indirect connection of a binding agent to a buoyant label, via the linkers, to form a buoyant reagent. In certain embodiments, the at least one first linker moieties are functionally exposed avidin or streptavidin, and the second linker moieties are biotin or a biotin derivative, either alone or linked with oligonucleotide binding pairs as described herein.

In other embodiments, the first linker is a first oligonucleotide and the second linker is a second oligonucleotide complementary over at least a portion of its length (such as fully complementary) to the first oligonucleotide and capable of binding to the first oligonucleotide via base pairing.

In certain embodiments, a combination of two or more different buoyant labels are employed, one or more of these having a density substantially greater than the density of the liquid medium and one or more having a density substantially less than the liquid medium. The one or more binding agents attached to the one or more different buoyant labels may target one or more different molecular targets or may all target the same molecular target, and the one or more molecular targets may be on the desired cells or the undesired cells.

In certain embodiments, the quantity of the one or more binding agents added to the host liquid in binding agent-first order is sufficient to substantially saturate the binding agent's binding sites on the target cells of the cell suspension while leaving only an amount of unbound binding agent remaining in the mixture that is insufficient to substantially interfere with the binding of buoyant label to the cell-bound binding agent, thus obviating the need to remove unbound binding agent prior to adding buoyant label.

In further embodiments, the quantity of the one or more binding agents to add to the host liquid is determined by a preceding count of the number of target cells present in the host liquid, employing any suitable means known to those skilled in the art, for example, without limitation a hematology analyzer, flow cytometry, microscopy, sedimentation, enzymatic assay, ELISA, or the like. In certain embodiments, the quantity of the one or more binding agents to add to the host liquid is determined by testing a range of two or more quantities of binding agents against aliquots of a host liquid. In further embodiments, the quantity of the one or more binding agents used is up to 40 times the number of binding agent binding sites present on the target cells.

The various binding agents, linkers, and buoyant labels may be collectively referred to as "buoyancy-activated cell sorting reagents" (BACS reagents).

The buoyant reagents may be produced by any suitable combination of the buoyant labels and binding agents/optional linkers including, but not limited to, manufactured buoyant reagents, secondary buoyant reagents, binding agent-first order buoyant reagents, buoyant-first order buoyant reagents, and simultaneous buoyant reagents. As used herein, a "manufactured buoyant reagent" is a buoyant reagent wherein the buoyant label and the binding agent are attached to each other to form a buoyant reagent prior to contacting the host liquid.

As used herein, a "secondary buoyant reagent" is a buoyant reagent, which spontaneously assembles when host liquid is contacted with a buoyant label and a separate binding agent. Thus, in some embodiments, the buoyant reagents comprise secondary buoyant reagents that assemble within the host liquid, wherein prior to processing the host liquid to generate attached target cells, the method further comprises preprocessing steps comprising contacting the host liquid with buoyant labels and binding agents for a time and under conditions suitable to promote attachment of the binding agents to the buoyant labels to produce the buoyant reagents. Any suitable order of addition of the buoyant label and separate binding agent to the host liquid can be employed as suitable for an intended purpose. As used herein, "binding agent-first order" is an order of forming a secondary buoyant reagent by contacting the host liquid first with the binding agent, and then subsequently contacting the cell suspension with the buoyant label. As used herein, "buoyant-first order" is an order of forming a secondary buoyant reagent by contacting the host liquid first with the buoyant label, and then subsequently contacting the host liquid with the binding agent. As used herein, "simultaneous order" is an order of forming a secondary buoyant reagent by contacting the host liquid substantially simultaneously with both the buoyant label and the binding agent.

In one non-limiting embodiment, (i) each binding agent comprises (A) a primary binding agent comprising an agent capable of binding to at least one cellular epitope on the target cells, (B) a first linker bound to the primary binding agent, wherein the first linker comprises a first oligonucleotide having a first complementary region; and (ii) each buoyant label comprises a second linker bound to the buoyant label;

wherein the second linker comprises a second oligonucleotide having a second complementary region, wherein the second complementary region is perfectly complementary to the first complementary region, and wherein a hybrid of the first and second complementary regions has a calculated Tm of at least 40° C.;

wherein the preprocessing step comprises contacting the host liquid with the buoyant labels and the binding agents for a time and under conditions suitable to promote hybridization of the first and second complementary regions to produce the buoyant reagents;

wherein the processing comprises contacting the target cells and the buoyant reagents in the host liquid under conditions suitable to generate the attached target cells; and wherein the method further comprises:

(d) subjecting the attached target cells to a temperature of 37° C. or less within the functionally closed system after step (c) for a time sufficient to dehybridize the first complementary region and the second complementary region to release the buoyant reagents from the target cells.

In another aspect, the invention provides cell separation methods, comprising:

(a) providing a host liquid, wherein the host liquid comprises attached target cells, wherein each attached target cell comprises
  (i) a binding agent bound to at least one cellular epitope on a target cell,
  (ii) a first linker bound to the agent, wherein the first linker comprises a first oligonucleotide having a first complementary region;
  (iii) a buoyant label comprising a second linker bound to the buoyant label, wherein the second linker comprises a second oligonucleotide having a second complementary region, wherein the second complementary region is perfectly complementary to the first complementary region, wherein the second complementary region is hybridized to the first complementary region to form a hybrid, and wherein the hybrid of the first and second complementary regions has a calculated Tm of at least 40° C.;

(b) applying a vectorial force, such as centrifugation, to the host liquid to cause the attached target cells to stratify within the host liquid;

(c) sequestering the attached target cells; and (d) subjecting the attached target cells to a temperature of 37° C. or less after step (c) for a time sufficient to dehybridize the first complementary region and the second complementary region to release the buoyant labels from the target cells.

In this aspect, the methods may be carried out in a functionally closed system, or may be carried out in an open system. The methods may be carried out in any suitable volume. In one embodiment of this aspect, the methods are carried out in volumes of at least 1 ml, 2 ml, 5 ml, 10 ml, 25 ml, 50 ml, 100 ml, or at least 200 ml.

In one embodiment, the attached target cells are generated prior to step (a) by processing steps comprising contacting target cells in the host liquid with manufactured buoyant reagents comprising the binding agent, the first linker, and the second linker, wherein the second complementary region is hybridized to the first complementary region to form the hybrid;

wherein the contacting is carried out for a time and under conditions suitable to promote attachment of the cells to one or more of the manufactured buoyant reagents to generate the attached target cells. In another embodiment, the attached target cells are generated prior to step (a) by processing steps comprising:

(A) contacting the host liquid with the buoyant labels and binding agents bound to the first linker for a time and under conditions suitable to promote hybridization of the first and second complementary regions to produce buoyant reagents; and (B) contacting the target cells and the buoyant reagents in the host liquid for a time and under conditions suitable to generate the attached target cells In these different embodiments/aspects, the first oligonucleotide comprises a first complementary region that is perfectly complementary to a second complementary region in the second oligonucleotide. As will be understood by those of skill in the art, the first and second oligonucleotides may comprise additional nucleotides as suitable for an intended purpose (for example, to bind the oligonucleotide to another component of the linker, such as biotin or streptavidin). In this embodiment, the hybridized complementary oligonucleotides link binding agents (such as antibodies) to the buoyant label (such as gas filled bubbles) in a reversible fashion, enabling the release of target cells from their bound bubbles by raising the temperature of the cell suspension sufficiently to dehybridize the hybrid formed between the first and second complementary regions. The inventors have surprisingly discovered that hybrids with a theoretical Tm of 40° C. or greater can be used in the methods of the invention, even though such high temperatures, if they were required to achieve detachment of bubbles from isolated target cells, would be expected to compromise the viability of most mammalian cell types (which prefer a maximum of 37° C.). Surprisingly, the inventors discovered that the hybrids with a theoretical Tm of 40° C. or greater effectively releases bubbles from cells at well below the calculated Tm, i.e.: at about 37° C. While not being bound by any mechanism, the inventors believe that release well below the theoretical Tm is due to the large Brownian, centripetal, and/or frictional forces imposed on these hybrids by the micrometer-diameter cells and bubbles which they tether together, which may weaken the hybrids below their theoretical Tm. As a consequence the inventors have routinely achieved 97% to 99% target cell viability in these embodiments, with recovery efficiency of up to 90%.

In one embodiment, the hybridization step can be carried out at temperatures ranging from 4° C. to about 30° C. In various further embodiments, the hybridization step can be carried out at temperatures ranging from 10° C. to about 30° C., 15° C. to about 30° C., 20° C. to about 30° C., 21° C. to about 30° C., 22° C. to about 30° C., 23° C. to about 30° C., 24° C. to about 30° C., 25° C. to about 30° C., 10° C. to about 25° C., 15° C. to about 25° C., 20° C. to about 25° C., 21° C. to about 25° C., 22° C. to about 25° C., 23° C. to about 25° C., or 24° C. to about 25° C.

In these embodiments, the calculated Tm is the Tm as calculated using the nearest-neighbor two-state model:

$$Tm(°C.) = \frac{\Delta H°}{\Delta S° + R\ln[oligo]} - 273.15$$

where $\Delta H°$ (enthalpy) and $\Delta S°$ (entropy) are the melting parameters calculated from the sequence and the published nearest neighbor thermodynamic parameters under the ionic conditions used, R is the ideal gas constant (1.987 calK$^{-1}$ mole$^{-1}$), [oligo] is the molar concentration of an oligonucleotide, and the constant of −273.15 converts temperature from Kelvin to degrees of Celsius. The nearest neighbor thermodynamic parameters are those of Allawi, H., Santa Lucia, J. Jr., Biochemistry, 36, 10581, and the monovalent cation correction is that of Owczarzy, R. et al., Biochemistry, 47, 5336

In various embodiments, the calculated Tm of the hybrid between the first complementary region and the second complementary region is between 40° C. and about 60° C., between 40° C. and about 58° C., 40° C. and about 56° C., 40° C. and about 55° C., 40° C. and about 54° C., 40° C. and about 53° C., 40° C. and about 52° C., 40° C. and about 51° C., 40° C. and about 50° C., 41° C. and about 60° C., between 41° C. and about 58° C., 41° C. and about 56° C., 41° C. and about 55° C., 41° C. and about 54° C., 41° C. and about 53° C., 41° C. and about 52° C., 41° C. and about 51° C., 41° C. and about 50° C., 42° C. and about 60° C., between 42° C. and about 58° C., 42° C. and about 56° C., 42° C. and about 55° C., 44° C. and about 54° C., 42° C. and about 53° C., 42° C. and about 52° C., 42° C. and about 51° C., or 42° C. and about 50° C.

As will be understood by those of skill in the art, the specific nucleotide sequence of the first and second complementary regions may be any that forms perfect complements over the length of the first and second complementary regions, resulting in a hybrid having a calculated Tm as recited.

A "vectorial force" is a force having a direction as well as a magnitude, including but not limited to gravitational force, centripetal force, and centrifugal force.

Those of skill in the art are well aware of the relative densities of the main cellular components of blood, the Cluster of Differentiation (CD) surface markers on specific cell types and the relationship of those cell types to various medical treatment indications.

The methods of the invention can be carried out in any suitable, functionally closed cell separation system. In one non-limiting embodiment, the cell separation system may comprise the system described in U.S. Pat. No. 8,747,289. In an improved embodiment, the cell separation device comprises the functionally closed cell separation system of any embodiment or combination of embodiments of the systems disclosed herein. In one such embodiment, the functionally closed system comprises a cell separation system comprising
  (a) a cartridge comprising
    (i) a processing container comprising at least one input port, a first exit port, and a second exit port;
    (ii) two or more additional containers, comprising at least a second container comprising an input port; and a third container comprising an input port and a first exit port;
    (ii) a first conduit connecting the first exit port of the processing container and the input port of the second container, wherein the first conduit comprises a first reversible closing device, wherein the second container is transiently fluidically connected to the processing container such that fluid flow only from the processing container to the second container may occur when the first reversible closing device is opened;
    (v) a second conduit connecting the second exit port of the processing container and the input port of the third container, wherein the second conduit comprises a second reversible closing device, wherein the third container is transiently fluidically connected to the processing container such that fluid flow only from the processing container to the third container may occur when the second reversible closing device is opened;
  (b) a transfer container comprising at least one port;
  (c) an at least third conduit connecting
    (i) the first exit port of the third container to the at least one port of the transfer container, and
    (ii) the at least one port of the transfer container to the at least one inlet port of the processing container
  wherein the at least third conduit comprises at least a third reversible closing device, such that (A) the third container is transiently fluidically connected to the transfer container, and (B) the transfer container is transiently fluidically connected to the processing container; wherein the at least third conduit is configured such that only one of the following may be true
    (I) fluid flow only from the third container to the transfer container may occur when the at least third reversible closing device is opened; or
    (II) fluid flow only from the transfer container to the processing container may occur when the at least third reversible closing device is opened.

As used herein, a "reversible closing device" is any device that can be closed (such as a by a controller) to prohibit fluid flow. Exemplary such devices include, but are not limited to valves, clamps, and stopcock.

As used herein, "cartridge" is a closed housing (having a roof) that allows the aseptic transfer of cells between containers within the closed housing and the mixing of cells, binding agents, buoyant labels, and buoyant reagents to accomplish linkage, comprising three or more mechanically joined containers which are transiently fluidically connected. As used herein, "transiently fluidically connected" means that the containers are fluidically non-continuous (that is, each functionally closed) other than when transiently connected via opening of the device's normally closed valves to achieve aseptic transfer of fluid or cell suspension from one container to another. The "transfer container" is transiently fluidically coupled to the third container via the second conduit, and transiently fluidically coupled to the processing container, but there is no requirement that the transfer container be mechanically coupled to the cartridge, except via the relevant conduit.

The "conduits" may be any suitable device to permit fluid transfer between the containers, including but not limited to tubing. All of the conduits are "normally closed", such that the containers are not fluidically connected. The conduits may be closed by any suitable reversible closing device, such as a valve, clamp or stopcock. In one embodiment, the conduits within the cartridge may be closed by a spring loaded, tube pinching mechanism at all times except when fluids should pass, at which time the pinching mechanism may be rotated (for example, by a control module automatically controlling the reversible opening of the conduit) to allow passage of the fluids, and then may be rotated again to close off that passage by re-pinching the conduit.

The third conduit between the exit of the third container to the transfer container and from the transfer container to the input of the processing container is also normally closed by any suitable reversible closing device. In one embodiment, the third conduit may be clamped on the exterior of the cartridge (just adjacent to the exit port of the third container) and may be unclamped at the time of transfer of sequestered attached cells from the third container to the transfer container (for example, by gravity draining the sequestered attached cells from the third container to the transfer container). Following transfer into the transfer container, the clamp on the third conduit adjacent to the third container port may be reestablished. At that time, for example, the sequestered attached cells may be transferred to the processing container via the third conduit (for example, by gravity draining the sequestered attached cells back into the processing chamber, for further processing—such as isolating/enriching a sub-population of the sequestered, attached cells, including but not limited to mononuclear cells to join the cell-free and platelet free plasma from the host liquid).

The transfer container may be mechanically coupled to the cartridge, or may be physically connected only via the relevant conduit connecting the transfer container to containers within the cartridge to maintain the system as a functionally closed system.

The various containers may comprise any suitable material, such as a rigid structure, a bag, a bottle, or any other suitable structure. In one embodiment, each container is a rigid container, such as a hard plastic container (including but not limited to polycarbonate). In another embodiment, the transfer container is a flexible container, including but not limited to a bag. The transfer container can be a rigid container, because the air in the container at the start of the transfer of harvested target cells in solution can displace along the relevant conduit connecting it to the processing container. The transfer container also can be a flexible container, which has the advantage of being foldable into a small shape to make it easier to store, for example, in the rotor compartment of a centrifuge during centrifugation.

In one embodiment, the processing container is an approximately conical central container, while the second and third containers are smaller, circumferentially located containers. The containers may be of any suitable volume for a given purpose.

Figure 9:
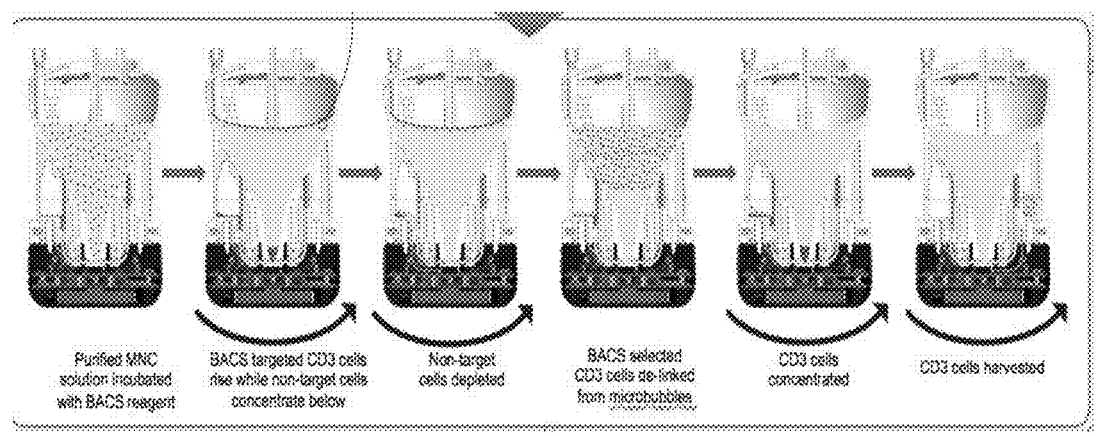
FIG. 9 shows an exemplary flow chart of an embodiment of the invention in which the desired cells are CD3+ cells, and the methods comprise using the cell separation system described herein.

In one embodiment, the third and second containers each may further comprise additional, normally closed ports providing optional points of connection to any suitable receiving containers external to the cartridge. In another embodiment, the processing, second, and third containers may share a common filtered air vent to provide air displacement as fluids move in and out of all the containers and the transfer container of the cartridge. In the normal operation of the cartridge this filtered air vent does not permit fluid transfer between the containers. FIG. 9 shows an exemplary flow chart of an embodiment of the invention in which the desired cells are CD3+ cells, and the methods comprise using the cell separation system described herein.

In another embodiment, the methods comprise contacting the target cells and buoyant labels for a time and under conditions suitable to promote attachment of the target cells to one or more of the buoyant labels to generate attached target cells. In one embodiment, each buoyant reagent comprises one or more second linkers, wherein the one or more second linkers are bound to one or more first linkers attached to at least one binding agent, wherein the at least one binding agent is capable binding to a cellular epitope on the target cell; and wherein the contacting comprises contacting the target cells and the buoyant reagents for a time and under conditions suitable to promote attachment of the target cells to one or more of the buoyant reagents to generate the attached target cells.

In this embodiment, the processing comprises generation of buoyant reagents within the functionally closed system; this can be done in the presence or absence of the target cells. In non-limiting embodiments, generation of buoyant reagents may be carried out by mixing:

(A) (i) firstly at least one binding agent capable of binding to at least one molecular target and bearing at least one first linker; (ii) secondly at least one buoyant label bearing at least one complementary linker; or (B) (i) firstly at least one buoyant label bearing at least one linker; (ii) secondly at least one binding agent capable of binding to the at least one molecular target and bearing at least one complementary linker; or (C) at least one buoyant label bearing at least one linker and at least one binding agent capable of binding to the at least one molecular target and bearing at least one complementary linker substantially simultaneously.

In another embodiment, the methods comprise generating target cell-binding agent complexes first, as follows:

(i) contacting the host liquid with primary binding agents, wherein each primary binding agent comprises (A) an agent capable of binding to at least one cellular epitope on the target cells, and (B) a first linker bound to the agent; wherein the contacting occurs under conditions suitable to promote attachment of the target cells to the primary binding agents to produce target cell-binding agent complexes; and (ii) incubating the target cell-binding agent complexes with the buoyant labels, wherein each buoyant label comprises a second linker, wherein the second linker is capable of binding to the first linker; wherein the incubating occurs under conditions suitable to promote binding of the first linker to the second linker to generate the attached target cells.

In this embodiment, the method may comprise no intermediate step of removing unbound primary binding agents occurs between steps (i) and (ii). This embodiment may be referred to as a "no-wash" protocol. As shown in the examples that follow, the no-wash protocol routinely yielded excellent target cell recoveries (from 70+% to 90+%) across a wide variety of source materials, cells concentrations, process volumes, targets, manual or automated protocols, and buoyant reagent (such as gas-filled bubble) diameters. The successful application of the no-wash protocol across many source materials and process conditions is a surprising result. Workers normally skilled in the art of physical capture of target cells using binding agents (such as antibodies) and particles (such as microbeads, nanoparticles, or microbubbles) know that without detailed preliminary antibody titration studies (on each independent biological specimen) it is impossible to predict the total number of antibody binding sites in a given target cell suspension. In the absence of such titration studies (which are time-consuming and consume source material), adding a standard quantity of antibody may be expected to sometimes result in a substantial excess of not-cell-bound antibody remaining in the cell suspension, which would be expected to compete with cell-bound antibody for binding to particles in said second step, thus resulting in low target cell recovery efficiency. The no-wash protocol confers valuable benefits. Normally, in order to spare the end-user the requirement of a wash step, a manufacturer would pre-label particles with binding agents, such as antibodies, during manufacturing. This transfers the typically requisite wash step from the end-user to the manufacturer, increasing manufacturing costs (and thus reagent prices). Manufacturers employing this strategy are also presented with the requirement of assembling and stocking a large number of different antibody-labeled microbubble products (one for each distinct target molecule of interest to customers). This leads to complex manufacturing processes and inventories of numerous distinct products, again increasing manufacturers' costs and thus product prices. Also, in the common case where the buoyant reagent component of a labeled buoyant reagent product has a shorter inherent shelf lives than does the binding agent component, this also leads to wastage of expensive binding agents as inventory expires, again increasing costs.

In another embodiment, a manufactured buoyant reagent capable of binding to the at least one molecular marker can be used. In each of these embodiments, the mixing of buoyant reagents and target cells can be carried out in the transfer container, the processing container, or both.

In one embodiment, the buoyant reagents are generated in the transfer container. In other embodiments, the buoyant reagents may be generated in the processing chamber, or in an external mixing device.

In a further embodiment, contacting the buoyant reagents with the target cells to produce the attached target cells is carried out in the transfer container.

Mixing of the BACS regents and target cells in solution can be accomplished via any suitable means that accounts for the fact that the buoyant labels rise while target cells will fall in the host liquid. In one embodiment, the mixing is carried out so that substantially every binding site on every target cell is bound with a buoyant label, to improve efficiency. In one non-limiting embodiment, mixing is carried out by providing nutating motion to the BACS reagent and the solution of target cells in the processing container of the cartridge, such as by placing a device of the invention on a rotating or shaking platform. In a further embodiment, the mixing comprises periodic re-orienting of the cartridge by 180 degrees to reverse the intrinsic rising motion of the buoyant label and lowering motion of the target cells to move toward the opposite interior surfaces of the processing container.

In another non-limiting embodiment, mixing is carried out by providing nutating motion to the BACS reagent and the target cells in solution in the transfer container. In a further embodiment, the mixing comprises periodic re-orienting of the transfer container by 180 degrees to cause the intrinsic rising motion of the buoyant label and falling motion of the target cells to move toward the opposite interior surfaces of the transfer container.

In further non-limiting embodiments, the mixing is carried out by using a cell separation system comprising an on-board mixer. Embodiments of such on-board mixers are described below, in further disclosure relating to the cell separation system.

In another embodiment, the host liquid to be processed is a depleted host liquid, and prior to the processing or the preprocessing steps, the method comprises applying a vectorial force, such as centrifugation, to non-depleted host liquid within the functionally closed system, such as within the processing container, to deplete non-desired cells, such as by passing the non-desired cells into the second container, thus producing the depleted host liquid to be processed. This embodiment permits the steps of depletion of non-desired cells and subsequent purification of target/desired cells to be carried out in the same functionally closed system, which was not possible using prior art methods. In the two-step process, the initial step of enrichment increases the relative abundance of cells of interest versus cells not of interest, to levels sufficiently greater than that of the starting material to permit subsequent processing to proceed efficiently. In a specific embodiment this enrichment step is performed via differential centrifugation in any embodiment or combination of embodiments of the systems described herein. In the second step, the output cell suspension of the initial (enrichment) step is subjected to the processing steps using the buoyant reagents to achieve recovery of as many target cells as possible, of sufficient purity for their intended application (i.e., contaminated by as few not-of-interest cells as required). In the two-step process, it is often the case that some cells of interest are lost during the initial enrichment step. Hence there is here also an overall recovery metric: percentage of target cells present in the starting material that are recovered in the output of the BACS step.

As will be understood by those of skill in the art, the application of the vectorial force may be carried out a single time to remove non-desired cells from the host liquid, or two or more differential centrifugation steps may be carried out to sequentially remove non-desired cells. An example of this process can be seen in FIG. 10.

As will be understood by those of skill in the art, producing the depleted host liquid may comprise application of a single round of applying vectorial force, such as centrifugation, to the non-depleted host liquid within the functionally closed system, such as within the processing container, to deplete non-desired cells.

Figure 10:
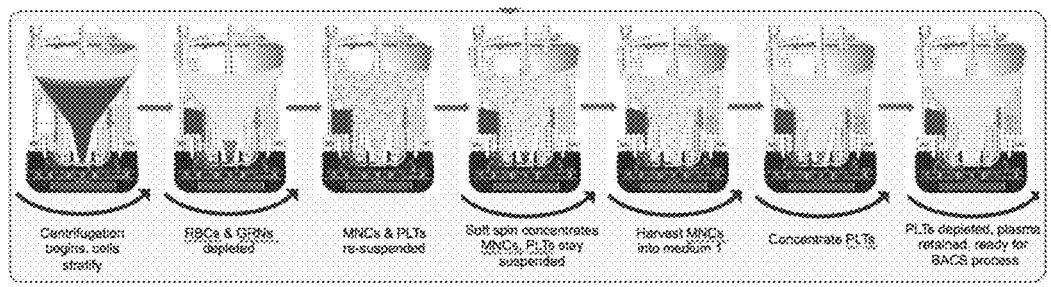
FIG. 10 shows an exemplary flow chart of an embodiment of the invention in which two or more differential centrifugation steps are carried out to sequentially remove non-desired cells.

Alternatively, depleting the host liquid may comprise two or more rounds of applying the vectorial force (such as centrifugation) to remove different types of non-desired cells to produce the depleted host liquid to be further processed to isolate the desired target cells (FIG. 10). For example, when the host liquid is whole blood, a first round of centrifugation may be used to deplete, for example, red blood cells only, or red blood cells and granulocytes, with a second round of centrifugation to stratify mononuclear cells and platelets to form the depleted host liquid.

In one non-limiting embodiment, the functionally closed system can receive a host liquid (such as normal blood) that comprises a source of desired cells, into the processing container and, when placed in a centrifuge, will perform an initial desired cell enrichment step during centrifugation, including transfer of non-desired cells (such as RBCs, GRNs and PLTs) to the second container within the cartridge and provide aseptic transfer of the enriched desired cell preparation (such as MNCs) including the rare desired cells from the third container and then back into the processing container for subsequent further purification via binding to the buoyant labels and isolation as described above. The non-desired cells such as RBCs, GRNs, PLTs and excess fluid (such as plasma) can be removed from the functionally closed system without disturbing the enriched target cells, all while the system remains functionally closed.

In one embodiment, the depleted host liquid is passed from the processing container to the transfer container and mixed with the buoyant reagents to initiate processing step (a) to produce the attached target cells. In a further embodiment, the method further comprises detaching the buoyant label from the target cells within the functionally closed system to produce detached target cells. Any suitable method to detach the buoyant label from the target cells can be used including, but not limited to, disruption of the buoyant reagents (for example, via the application of positive or negative pressure or ultrasonic energy that will not damage the cells), or by breaking the linkages between the binding agents bound to the target cells and the buoyant labels those binding agents are linked to (for example via dehybridization of oligonucleotide linkers or enzymatic cleavage of macromolecular linkers or chemical cleavage of small-molecule linkers), thus releasing the target cells to, for example, migrate down the conical processing container of the cartridge (now substantially free of non-target cells) during centrifugation, to be positioned for collection into the cartridge's third container. In certain embodiments, the device for applying said energy or pressure (such as a sonicator) is integral to the functionally closed cell separation system. In certain other embodiments, the device for applying said energy or pressure is integral to one of the containers of the system. In certain embodiments, said energy or pressure is separate from any container of the system. The inventors have surprisingly routinely obtained high target cell viabilities (90% to 100%), coupled with high target cell recovery efficiency, using sonication for detaching the target cells from the buoyant reagents.

In certain embodiments, the method is employed to achieve positive selection. In this embodiment, the target cells are the desired cells, and the method further comprises concentrating the detached target cells within the functionally closed system, wherein the sequestering comprises passing the concentrated detached target cells to the third container. In other embodiments, the method is employed to achieve negative selection (i.e.: the target cells are not the desired cells). In this embodiment, the sequestering comprises concentrating the detached target cells within the functionally closed system. In certain other embodiments, two or more rounds of negative and/or positive selection are employed sequentially. In certain embodiments, employing two or more sequential rounds of selection, cells are directed from either the second or third container back to the processing container, with or without mixing of the directed cells with additional BACS reagents.

In another embodiment, the cell separation system further comprises a control module for controlling the activity in at least the cartridge and the first and second conduits.

In some embodiments, the controller may also control activity within the transfer container and/or within the third conduit. For example, the controller may control activity within the transfer container and/or within the third conduit in embodiments in which the transfer container is present within the cartridge. The controller may control the reversible closing devices that direct the flow of fluid between the cartridge containers, such as during centrifugation. In one non-limiting embodiment, the cartridge containing the target cell/buoyant label mixture is centrifuged so that target cells that bind to the buoyant label separate from the cells not bound to the buoyant label. The control module may be programmed to deliver the non-buoyant pelleted cells to the second container of the cartridge via the first reversible closing device, leaving the bulk of the supernatant and substantially all of the target cells that bound to the buoyant reagent in the processing container of the cartridge.

In a further embodiment, the processing container or other containers may optionally be interrogated by at least one detector for detecting the presence or absence of cells. In this embodiment, the control module controls opening and closing of the reversible closing devices within at least the first and/or second conduits based on information relayed from the at least one detector. Any suitable detector may be used, including but not limited to optical detectors.

In all embodiments described herein, the desired cells may be any cells of interest, including but not limited to hematopoietic stem and progenitor cells, mesenchymal stem and progenitor cells, adipose-derived stem and progenitor cells, endothelial progenitor cells found in normal blood, placental/cord blood, bone marrow, white blood cells, granulocytes, mononuclear cells, lymphocytes, monocytes, T-cells, B-cells, NK cells, the stromal vascular fraction cells resident in adipose tissue, cultured cells, genetically modified cells, and sub-populations of such target cells. In various non-limiting embodiments, the desired cells may be CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells. This list includes negative markers (indicated by a superscript minus sign), where the methods are used to purify cells negative for the recited marker. The negative markers provided in this list are pluripotency markers, and thus depleting cells having one or more of these negative markers can be used to deplete differentiated cells of residual pluripotent cells (i.e., iPSCs or ESCs).

In various embodiments, the host liquid has a volume of at least 10 ml (or, alternatively, at least 25 mL, at least 50 mL, at least 75 mL, at least 100 mL, at least 200 mL, etc.).

In other embodiments, the desired cells represent less than 10% (or, alternatively, less than 5%, 1%, 0.5%, 0.1%, 0.05%, etc.) of the cells in the non-depleted host liquid. In one non-limiting embodiment, CD3+, CD4+, CD14+, CD19+, CD56+, or CD34+ cells are the desired cells and represent less than about 0.2% in the non-depleted host liquid (whole blood), and represent than about 20%, 18%, 15%, 12%, 10%, 5%, 2.5%, 1%, or 0.5% of cells in depleted host liquid (such as whole blood after red blood cell and/or platelet depletion)

In still further embodiments, a recovery efficiency of the desired cells is greater than 68%, or greater than 75%, or greater than 80%, or greater than 85%, or greater than 90%, or greater than 95%. In one non-limiting embodiment, CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells are the desired cells and have recoveries greater than 68%, or greater than 75%, 80%, 85%, or 90%.

In other embodiments, viability of the desired cells is greater than 90%, or greater than 95%, or greater than 97%, or greater than 99%. In one non-limiting embodiment, CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells are the desired cells and have viabilities greater than 90%, or greater than 91%, 92%, 93%, 94%, 95%, 96%, 97%, 98%, or 99%.

In further embodiments, the desired cells are present at between about $5 \times 10^3$ desired cells/mL and about $2.5 \times 10^8$ desired cells/mL in the unprocessed host liquid. In various further embodiments, the desired cells may be present at between about $5 \times 10^3$ desired cells/mL and about $2.5 \times 10^7$ desired cells/mL; $5 \times 10^3$ desired cells/mL and about $2.5 \times 10^6$ desired cells/mL, $5 \times 10^3$ desired cells/mL and about $2.5 \times 10^5$ desired cells/mL, $5 \times 10^3$ desired cells/mL and about $10^5$ desired cells/mL, and about $5 \times 10^3$ desired cells/mL and about $5 \times 10^4$ desired cells/mL in the unprocessed host liquid.

For example, when CD34+ cells are the desired cells and cord blood is the host liquid, the desired cells may be present at between about $5 \times 10^3$ desired cells/mL and about $5 \times 10^4$ desired cells/mL in the unprocessed cord blood, or at about $5 \times 10^3$ desired cells/mL in the unprocessed cord blood.

In a further non-limiting example, CD3+ cells are the desired cells and a leukapheresis product is the host liquid, the desired cells may be present at between about $2.5 \times 10^7$ desired cells/mL and about $2.5 \times 10^8$ desired cells/mL. In another non-limiting example, CD3+ cells are the desired cells and are present between about $3 \times 10^6$/mL and about $6 \times 10^6$/ml in the unprocessed host liquid (whole blood).

In certain embodiments, the total cell processing time employing the methods of the invention is less than one hour, less than 45 minutes, less than 30 minutes, less than 25 minutes, less than 20 minutes, less than 15 minutes, less than 10 minutes, or less than 5 minutes.

In certain embodiments, appropriate containers of the functionally closed system (such as the processing container, the second container, and/or the transfer container) are purged with a gas mixture containing sufficient $O_2$ and $CO_2$ to meet the metabolic needs of the cells, the balance of the gas mixture being the same perfluorocarbon gas contained in the buoyant agents (such as microbubbles).

In certain embodiments, the host liquid in which the target cells are suspended is equilibrated with a gas mixture containing sufficient $O_2$ and $CO_2$ to meet the metabolic needs of the cells, the balance of the gas mixture being the same perfluorocarbon gas contained in the in the buoyant agents (such as gas-filled bubbles). It is well within the level of those of skill in the art to determine suitable conditions to be employed in carrying out the methods of the invention based on the disclosure herein.

In another aspect, the invention provides cell suspensions comprising
(a) a liquid medium having a volume of at least 10 mL (or, alternatively, at least 25 mL, at least 50 mL, at least 75 mL, at least 100 mL, at least 200 mL, at least 400 mL, at least 800 mL, etc.); and
(b) desired cells suspended in the liquid medium, wherein the desired cells are selected from the group consisting of hematopoietic stem and progenitor cells, mesenchymal stem and progenitor cells, endothelial progenitor cells found in normal blood, placental/cord blood, bone marrow, white blood cells, granulocytes, mononuclear cells, lymphocytes, monocytes, T-cells, B-cells, NK cells, the stromal vascular fraction cells resident in adipose tissue, and sub-populations of such desired cells, wherein the desired cells are present in a liquid medium and wherein the desired cells make up at least 80% (or alternatively, at least 85%, 90%, 95%, 98%, 99%, or more) of cells in the cell suspension;
wherein the desired cells viability is greater than 90%, or greater than 95%, or greater than 97%, or greater than 99%; and
wherein the cell suspension is present within a closed cell separation system.

The cell suspensions of the invention are those desired cells obtained after sequestration (and optionally after cell detachment), but still either (a) contained within functionally closed system (such as the cell separation system), or (b) obtained directly from the functionally closed system prior to any downstream processing that might be carried out. The liquid medium is the liquid medium in which the cells are suspended after sequestration/cell detachment, and thus may be any such liquid medium suitable for a particular intended use. In various embodiments, the liquid medium may comprise saline, cell culture medium, or any other liquid medium suitable for a particular use. In one embodiment, the cell suspension is directly obtained from the closed cell separation system. In another embodiment, the cell separation system comprises the cell separation system/apparatus of any embodiment or combination of embodiments of the present invention. In a further embodiment, the cell suspension is present in a cell suspension removal stream via the transfer container of the closed cell separation system. In one embodiment, the desired cells in the composition comprise a buoyant label attached to the cells.

In one embodiment, the number of viable desired cells is at least $1\times10^3$, or at least $1\times10^4$, or at least $2\times10^4$, or at least $5\times10^4$, or at least $1\times10^5$, or at least, $2\times10^5$, or at least $5\times10^5$, or at least $1\times10^6$, or at least $2\times10^6$, or at least $5\times10^6$, or at least $1\times10^7$, or at least $2\times10^7$, or at least $5\times10^7$, or at least $1\times10^8$, or at least $2\times10^8$, or at least $5\times10^8$, or at least $1\times10^9$, or at least $2\times10^9$, or at least $5\times10^9$. In a further embodiment, the desired cells comprise buoyant labels attached to the cells. In a further embodiment, the cell suspension is present within a transfer container, a processing container and/or a third container of the cell separation system as recited in any embodiment or combination of embodiments disclosed herein.

In another aspect, a kit is provided comprising one or more binding agents, and/or one or more buoyant labels, and/or one or more buoyant reagents, and one or more cartridges and/or more one or more systems and/or one or more buffers.

In another aspect, the invention provides compositions comprising:
(a) at least one binding agent covalently or non-covalently linked to at least one first linker, the at least one binding agent able to bind to at least one molecular target on the cells in a cell suspension; and
(b) at least one buoyant label covalently or non-covalently linked to at least one second complementary linker, the at least one buoyant label exhibiting a density substantially different from the density of the liquid medium in which the cells to be separated are suspended.

In another embodiment, wherein the at least one buoyant label includes, but is not limited to, a gas-filled bubble, a hollow polymer, a glass bead, a microporous bead with entrained gas, a droplet of an immiscible liquid, a solid of any shape, a liquid of any shape, a gold nanoparticle or a silver nanoparticle. In a further embodiment, the desired cells comprise various cell types, including but not limited to, hematopoietic stem and progenitor cells, mesenchymal stem and progenitor cells and endothelial progenitor cells found in normal blood, placental/cord blood, bone marrow or the stromal vascular fraction cells resident in adipose tissue, cultured cells or genetically modified cells.

In one embodiment, the compositions comprise
(a) at least one binding agent covalently or non-covalently linked to at least one first linker, the at least one binding agent able to bind to at least one molecular target on the cells in a cell suspension; and
(b) at least one buoyant label covalently or non-covalently linked to at least one second complementary linker, the at least one buoyant label exhibiting a density substantially different from the density of the liquid medium in which the cells to be separated are suspended.

In another embodiment, the compositions comprise:
(i) a primary binding agent comprising an agent capable of binding to at least one cellular epitope on a target cell;
(ii) a first linker bound to the agent, wherein the first linker comprises a first oligonucleotide having a first complementary region;
(iii) a buoyant label;
(iv) a second linker bound to the buoyant label, wherein the second linker comprises a second oligonucleotide having a second complementary region perfectly complementary to the first complementary region, wherein a hybrid of the first and second linkers' complementary regions has a calculated Tm of at least 40° C.;
wherein the first linker and the second linker are hybridized to each other. In one embodiment, the composition further comprises a target cell bound to the primary binding agent.

In another aspect, the invention provides kits comprising
(i) a primary binding agent comprising an agent capable of binding to at least one cellular epitope on a target cell;
(ii) a first linker bound to the agent, wherein the first linker comprises a first oligonucleotide having a first complementary region;
(iii) a buoyant label;

(iv) a second linker bound to the buoyant label, wherein the second linker comprises a second oligonucleotide having a second complementary region, wherein the second complementary region is perfectly complementarity to the first complementary region, and wherein a hybrid of the first and second complementary regions has a calculated Tm of at least 40° C.

These compositions and kits are useful, for example, in specific embodiments of the methods described above, where target cell detachment is carried out by dehybridization. In one embodiment the calculated Tm of a hybrid of the first and second complementary region is between 40° C. and about 60° C. In another embodiment, the calculated Tm is calculated using the nearest-neighbor two-state model:

$$Tm(^\circ C.) = \frac{\Delta H^\circ}{\Delta S^\circ + R\ln[oligo]} - 273.15$$

where $\Delta H^\circ$ (enthalpy) and $\Delta S^\circ$ (entropy) are the melting parameters calculated from the sequence and the published nearest neighbor thermodynamic parameters under the ionic conditions used, R is the ideal gas constant (1.987 calK$^{-1}$ mole$^{-1}$), [oligo] is the molar concentration of an oligonucleotide, and the constant of −273.15 converts temperature from Kelvin to degrees of Celsius. In a further embodiment, one of the first linker and the second linker further comprises biotin (optionally linked to a first member of an oligonucleotide hybridizing pair), and the other further comprises streptavidin (optionally linked to a second member of an oligonucleotide hybridizing pair). In various embodiments, the buoyant labels are selected from the group consisting of gas-filled bubbles, hollow polymers, glass beads, microporous based with entrained gas, droplets of an immiscible liquid, gold nanoparticles, and silver nanoparticles. In one specific embodiment, the buoyant labels comprise gas-filled bubbles. In another embodiment, the gas-filled bubbles comprise perfluorocarbon gas cores encompassed by lipid, phospholipid, protein or carbohydrate shells. In a further specific embodiment, the gas-filled bubbles comprise perfluorocarbon gas cores encompassed by phospholipid shells. In a further specific embodiment, the gas-filled bubbles have a diameter between about 1 um and about 6.5 um.

In one embodiment, the at least one binding agent includes, but is not limited to, antibodies, oligonucleotides, aptamers, molecularly imprinted polymers, carbohydrates, proteins, peptides, enzymes, small molecules, lipids, fatty acids, metal atoms, metal ions or synthetic polymers. In another embodiment, the at least one first linker and/or the second linker includes, but is not limited to, biotin, avidin, streptavidin, an oligonucleotide, an antibody-binding protein, a moiety bound by an antibody-binding protein, combinations thereof, or any second attached binding agent. In a specific embodiment, the primary binding agent comprises an antibody.

In another aspect, the invention provides compositions comprising desired cells purified via buoyancy-activated cell sorting from a starting admixture of at least one molecular type of desired cell and at least one molecular type of non-desired cell where said starting admixture contains at least 1 times the number of non-desired cells as desired cells, or at least 5 times the number of non-desired cells as desired cells, or at least 10 times the number of non-desired cells as desired cells, or at least 50 times the number of non-desired cells as desired cells, or at least 100 times the number of non-desired cells as desired cells, or at least 500 times the number of non-desired cells as desired cells, or at least 1000 times the number of non-desired cells as desired cells wherein:

the recovery efficiency of the at least one type of desired cell is greater than 80%, or greater than 85%, or greater than 90%, or greater than 95%; the purity of the at least one type of desired cell is greater than 80%, or greater than 85%, or greater than 90%, or greater than 95%;

the viability of the at least one type of desired cell is greater than 90%, or greater than 95%, or greater than 97%, or greater than 99%; and the volume of the admixture of at least one molecular type of desired cell and at least one molecular type of non-desired cell subjected to buoyancy-activated cell sorting is greater than 2 mL, or greater than 10 mL, or greater than 50 mL, or greater than 100 mL, or greater than 150 mL, or greater than 200 mL, or greater than 400 mL, or greater than 800 mL.

In various embodiments, the purified desired cells, or cells expanded from the purified desired cells, are used for cell therapy, research, or drug discovery. In another embodiment, the desired cells are enriched via centrifugation prior to purification via buoyancy-activated cell sorting. In a further embodiment, the buoyancy-activated cell sorting step is performed in the same container in which the preceding desired cell enrichment was performed.

In various embodiments, the desired cells are expanded prior to purification, or subsequent to purification. In other embodiments, the cells are used for cell therapy, and the cell therapy is autologous or allogeneic. In further embodiments, the desired cells are stem or precursor cells, immune cells, differentiated from stem cells, differentiated from induced pluripotent stem cells, genetically engineered cells, and/or cells to be genetically engineered.

In various further embodiments, the desired cells are negatively selected via buoyancy-activated cell sorting, are positively selected via buoyancy-activated cell sorting, or a combination thereof. For example, the desired cells may be selected via buoyancy-activated cell sorting via a combination of sequential negative and positive selections, wherein the sequential negative and positive selections are performed in the same container.

Example 1

Isolation of Target Cells Using a Oligonucleotide Hybrid Linker

In order to prepare an enriched cell suspension-binding agent-buoyant label complex for use in the method of the present invention, the following protocol may be used: A peripheral blood mononuclear cell (PBMC) preparation was prepared by processing 200 ml of fresh human peripheral blood and a collected unit of placental cord blood. The PBMC preparation was diluted to a WBC concentration of 1×10$^7$/ml with PBSHE. The diluted PBMC preparation was enumerated using a Hematology Analyzer.

For CD3 Cell Isolation from Peripheral Blood PBMCs:

CD3 antibody and oligonucleotide hybrid was prepared by incubating CD3 antibody at 0.3 mg/mL (2 µM) concentration, previously conjugated at the 5' end to 20-Mer oligo 5'-GGA AGC GGT GCT ATC CAT CT-3' (SEQ ID NO:1) with $\frac{1}{10}^{th}$ volume complementary oligonucleotide (A') (4 µm concentration) of either 8-Mer, 10-Mer, 12-Mer or 14-Mer previously conjugated to biotin per 1 mL cell suspension. The complementary oligo sequence is the 3'-most bases of the 20-Mer oligo. Oligonucleotides were incubated at room temperature for one hour for hybridization to occur.

To the diluted PBMC preparation, 12.5 µg CD3 antibody-oligo hybrid was added per mL cell suspension (previously determined experimentally to be optimal for CD3+ cell selection) and incubated on a rotating mixer at room temperature for 20 minutes.

For CD34 Cell Isolation from Cord Blood PBMCs:

CD34 antibody and oligonucleotide hybrid was prepared by incubating CD34 antibody at 0.1 mg/mL (2 µM) concentration, previously conjugated at the 5' end to 20-Mer oligo 5'-GGA AGC GGT GCT ATC CAT CT-3' (SEQ ID NO:1) within $1/10^{th}$ volume complementary oligonucleotide (A') (4 µm concentration) of either 8-Mer, 10-Mer, 12-Mer or 14-Mer previously conjugated to biotin per 1 mL cell suspension. The complementary oligo sequence is the 3'-most bases of the 20-Mer oligo. Oligonucleotides were incubated at room temperature for one hour for hybridization to occur.

To the diluted PBMC preparation, 15 µg CD34 antibody-oligo hybrid was added per mL cell suspension (previously determined experimentally to be optimal for CD34+ cell selection) and incubated on a rotating mixer at room temperature for 20 minutes.

Separately, a buoyant reagent was prepared by briefly vortexing a vial of Advanced Microbubbles SIMB™ 4-5 to re-suspend the microbubbles; the concentration of the microbubble suspension was determined by analyzing a 2 µl aliquot on a MultiSizer™ 4 (Beckman Coulter). A ratio of 10 microbubbles per WBC was used to calculate the volume of microbubbles to be added to the PBMC suspension for CD3 isolation and a ratio of 50 microbubbles per WBC was used to calculate the volume of microbubbles to be added to the PBMC suspension for CD34 isolation. The PBMC-antibody-oligo hybrid-microbubble suspension was incubated on a rocking table at room temperature for 40 minutes.

Following incubation, the cell suspension was centrifuged at 400×g for 5 minutes. The microbubbles (and microbubble-bound cells) formed a cake floating on the meniscus (positive fraction), while unbound cells formed a pellet at the bottom of a container (negative fraction), and a clear solution was observed between the cell pellet and the bubble cake.

The positive fraction was transferred to a separate container to which a 30-fold excess of oligo A' was added and incubated in a waterbath at 37° C. for 20 minutes and then to a rotating mixer in a 37° C. incubator for 30 minutes to dehybridize the oligonucleotide. The microbubble-positive cell fraction was centrifuged at 400×g for 5 minutes. The now unbound target cell population formed a pellet at the bottom of the container whereas microbubbles formed cake floating on the meniscus. Microbubbes were removed from the container.

Diluted PBMC, negative fraction, positive fraction and microbubble samples were subjected to flow cytometric analysis. An antibody master-mix was used, containing FITC-labeled anti-human CD45, 7-aminoactinoamycin dye (7-AAD), and APC-labeled anti-human CD3 for CD3 isolation or PE-labeled anti-human CD34 for CD34 isolation. 50 µl aliquots of each cell suspension were added to flow tubes containing a volume of master-mix previously determined to be suitable. 50 µl of diluted PBMC suspension was added to both a positive control and a negative control flow tube. The positive control was labeled with master-mix, and the negative control tube was labeled with FITC-labeled anti-human CD45, 7-AAD, and PE or APC-labeled mouse IgG (isotype), All tubes were then vortexed and incubated for 20 minutes at room temperature in the dark. After this incubation, all tubes received 0.5 ml of 1× lysis buffer, then the tubes were vortexed and incubated at room temperature in the dark for an additional 10 minutes Immediately preceding flow cytometric analysis each tube received 50 µl of flow count bead suspension. The tubes were then analyzed using a CD45/7-AAD/CD3 gating strategy previously determined to yield adequate results with PBMCs for CD3 isolation or ISHAGE gating strategy for CD34 isolation.

Experimental results are displayed in FIG. 11. 8-Mer (n=1) and 10-Mer (n=1) and 12-Mer (n=1) oligonucleotide linkers with calculated Tm of 16.3° C., 27.9° C. and 41.6° C. yielded target cell recovery of 12.5% and 21.7% and 68.4% respectively. 14-Mer (n=3) oligonucleotide linkers with calculated Tm of 50.2° C. yielded target cell recovery between 76.7% and 94.5%. These results demonstrate that target cell recovery is a sensitive function of oligonucleotide linker length, and provide the surprising finding that highest recovery is achieved with oligonucleotide linker hybrids having a calculated Tm (under the ionic conditions employed) that is substantially higher than the dehybridization temperature of 37° C. (which is ideal for human cell viability) employed here. Under optimal conditions target cell recoveries of up to 95% were observed, which those skilled in the art will recognize exceed the recovery efficiency of conventional target cell isolation methods.

Example 2

Isolation of Target Cells from Human Blood in a Functionally Closed System

In order to prepare an enriched cell suspension-binding agent-buoyant label complex for use in the method of the present invention, the following protocol was used: Peripheral blood and leukapheresis mononuclear cell (PBMC) preparations were prepared by processing 200 ml of fresh human peripheral blood for CD3+ or CD4+ isolation and 100 mL leukapheresis for CD3+ isolation in the present invention and set to harvest 40-45 mL into PBSHE. After evacuation of the non-target cell fractions within the cartridges, the target cell enriched cell suspensions were transferred to the processing containers by means of the transfer container to maintain sterility.

For CD3+ Cell Isolation from Peripheral Blood:

PBMCs or leukapheresis PBMCs, 1 mL Biotinylated CD3 antibody (stock concentration 0.5 mg protein/mL) was diluted to a volume of 5 mL with PBSHE and added through an integrated 0.2 µm filter and incubated with constant mixing at room temperature for 20 minutes.

For CD4+ Cells from Peripheral Blood:

1 mL Biotinylated CD3 antibody (stock concentration 0.5 mg protein/mL) was diluted to a volume of 5 mL with PBSHE and added through an integrated 0.2 µm filter and incubated with constant mixing at room temperature for 20 minutes.

CD4+ Cells 0.5 mL Biotinylated CD3 antibody (stock concentration 0.5 mg protein/mL) was diluted to a volume of 5 mL with PBSHE and added through an integrated 0.2 µm filter and incubated with constant mixing at room temperature for 20 minutes.

Separately, a buoyant reagent was prepared by briefly vortexing 2×1.4 mL vials of Advanced Microbubbles SIMB™ 4-5 microbubbles for CD3+ or CD4+ and aseptically dispensing into a 5 mL syringe with a PVC output tube. The remainder of the 5 mL made up with PBSHE. Following completion of the 20 minute antibody incubation, the microbubble syringe was sterile welded to the 3rd conduit of the system and microbubbles added. The PBMC-antibodymicrobubble suspension was incubated with constant mixing at room temperature for 30 minutes.

Following incubation, the system was centrifuged at 400×g for 5 minutes. The microbubbles (and microbubble-bound cells) formed a cake floating on the meniscus, while unbound cells formed a pellet at the bottom of a container, and a clear solution was observed between the cell pellet and the bubble cake. The system was then centrifuged at 50×g for 1 minute to transfer the negative fraction to the second container, in this case serving as the depletion container. An aliquot of the negative was taken for cell enumeration The bubble cakes plus supernatant was transferred to the transfer container and then subjected to ultrasonic energy for 2 seconds, until bubbles were disrupted. The sonicated, positive cell fraction was transferred back to the processing container and centrifuged at 400×g for 5 minutes then transferred to the third container, in this case serving as the harvest container to a defined final volume. An aliquot of the positive fraction was taken for cell enumeration.

Diluted PBMC, negative fraction and positive fraction samples were subjected to flow cytometric analysis. An antibody master-mix was used, containing FITC-labeled anti-human CD45, 7-aminoactinoamycin dye (7-AAD), PE-labeled anti-human CD4 and APC-labeled anti-human CD3. 50 µl aliquots of each cell suspension were added to flow tubes containing a volume of master-mix previously determined to be suitable. 50 µl of diluted PBMC suspension was added to both a positive control and a negative control flow tube. The positive control was labeled with master-mix, and the negative control tube was labeled with FITC-labeled anti-human CD45, 7-AAD, and PE or APC-labeled mouse IgG (isotype), All tubes were then vortexed and incubated for 20 minutes at room temperature in the dark. After this incubation, all tubes received 0.5 ml of 1× lysis buffer, then the tubes were vortexed and incubated at room temperature in the dark for an additional 10 minutes. Immediately preceding flow cytometric analysis each tube received 50 µl of flow count bead suspension. The tubes were then analyzed using a CD45/CD4/7-AAD/CD3 gating strategy previously determined to yield adequate results with PBMCs.

Experimental results are shown in FIG. 12. Isolation of cells from peripheral blood yielded recovery of CD3+(n=4) between 80.9% and 88.1%, purity between 94.8% and 99.6% and viability between 90.7% and 95.8%. For CD4+ cells (n=1) recovery was 81.7%, purity 96.6% and viability 95.3%. Isolation of CD3+ cells from leukapheresis (n=1) yielded recovery of 83.0%, purity 98.6% and viability 96.1%. In each case, these combined recovery, purity, and viability metrics exceed those previously reported in the literature by workers employing entirely manual processes and open containers, demonstrating the improved performance of the present invention.

Example 3

Isolation of CD3+ Cells from Human Blood in a Functionally Closed System Using Oligonucleotide Linkers In order to prepare an enriched cell suspension-binding agent-buoyant label complex for use in the method of the present invention, the following protocol may be used: A peripheral blood mononuclear cell (PBMC) preparation was prepared by processing 200 ml of fresh human peripheral blood in the present invention and set to harvest 40-45 mL into PBSHE. After evacuation of the non-target cell blood fractions from the cartridge, the harvested enriched target cell suspension was transferred to the processing container via the transfer container to maintain sterility.

CD3 antibody and oligonucleotide hybrid was prepared by incubating 540 µg CD3 antibody at 3 mg/mL (2 µM) concentration, previously conjugated at the 5' end to 20-Mer oligo 5'-GGA AGC GGT GCT ATC CAT CT-3' (SEQ ID NO:1) within $\frac{1}{10}^{th}$ volume complementary oligonucleotide (A') (4 µm concentration) of 14-Mer previously conjugated to biotin. The complementary oligo sequence is the 3'-most bases of the 20-Mer oligo. Oligonucleotides were incubated at room temperature for one hour for hybridization to occur. Following hybridization antibody-oligo hybrid was added to PBMC through an integrated 0.2 µm filter and incubated with constant mixing at room temperature for 20 minutes.

Separately, a buoyant reagent was prepared by briefly vortexing 2×1.4 ml vials of Advanced Microbubbles SIMB™ 4-5 microbubbles and aseptically dispensing into a 5 mL syringe with a PVC output tube. The remainder of the 5 mL made up with PBSHE. Following completion of the 20 minute antibody incubation, the microbubble syringe was sterile welded to the 3rd conduit of the system and microbubbles added. The PBMC-antibody-microbubble suspension was incubated with constant mixing at room temperature for 30 minutes.

Following incubation, the system was centrifuged at 400×g for 5 minutes. The microbubbles (and microbubble-bound cells) formed a cake floating on the meniscus, while unbound cells formed a pellet at the bottom of a container, and a clear solution was observed between the cell pellet and the bubble cake. The system was then centrifuged at 50×g for 1 minute to transfer the negative fraction to the second container, the depletion container. An aliquot of the negative was taken for cell enumeration. Separately, a 600 µM concentration of competing Oligo-A' was combined in a 5 mL syringe with PBSHE.

The bubble cakes plus supernatant were transferred to the transfer container and the competing Oligo-A' was aseptically added. The PBMC-antibody-microbubble suspension was incubated with competing Oligo A' in a waterbath at 37° C. with constant mixing for 40 minutes.

The positive cell fraction was transferred back to the processing container and centrifuged at 400×g for 5 minutes then transferred to the third container, in this case serving as the harvest container, to a defined final volume. The unbound microbubbles remained in the processing container. An aliquot of the positive and microbubble fractions was taken for cell enumeration.

Diluted PBMC, negative fraction, positive and microbubble fraction samples were subjected to flow cytometric analysis. An antibody master-mix was used, containing FITC-labeled anti-human CD45, 7-aminoactinoamycin dye (7-AAD), and APC-labeled anti-human CD3. 50 µl aliquots of each cell suspension were added to flow tubes containing a volume of master-mix previously determined to be suitable. 50 µl of diluted PBMC suspension was added to both a positive control and a negative control flow tube. The positive control was labeled with master-mix, and the negative control tube was labeled with FITC-labeled anti-human CD45, 7-AAD, and APC-labeled mouse IgG (isotype), All tubes were then vortexed and incubated for 20 minutes at room temperature in the dark. After this incubation, all tubes received 0.5 ml of 1× lysis buffer, then the tubes were vortexed and incubated at room temperature in the dark for an additional 10 minutes Immediately preceding flow cytometric analysis each tube received 50 μl of flow count bead suspension. The tubes were then analyzed using a CD45/7-AAD/CD3 gating strategy previously determined to yield adequate results with PBMCs.

Experimental Results are Shown in FIG. 11.

Isolation of CD3+ cells from peripheral blood (n=1) using a 14-Mer oligonucleotide linker with a calculated Tm of 50.2° C. (n=1) yielded recovery of 76.7%, purity 97.3% and viability 96.8%. These results demonstrate that the oligonucleotide linker method yields excellent purity, recovery, and viability in an automated large-volume system while obviating the need for physical disruption of microbubbles (such as via sonication) in order to collect target cells, which could be difficult to control precisely in large-volume systems such as that employed here.

closed system, for a time and under conditions that promote attachment of the binding agents to the buoyant labels to produce the buoyant reagents.

3. The method of claim 2, wherein a hybrid of the first and second complementary regions has a calculated Tm of at least 40° C.; wherein the preprocessing step comprises contacting the host liquid with the buoyant labels and the binding agents for a time and under conditions that promote hybridization of the first and second complementary regions to produce the buoyant reagents;

wherein the processing comprises contacting the target cells and the buoyant reagents in the host liquid under conditions that generate the attached target cells; and

---

---

We claim:

1. A cell separation method, comprising:
(a) processing a host liquid having a volume of at least 10 mL in a functionally closed system,
wherein the host liquid comprises (i) target cells, and (ii) buoyant reagents comprising buoyant labels and binding agents,
wherein each binding agent comprises (A) a primary binding agent comprising an agent capable of binding to at least one cellular epitope on the target cells and (B) a first linker bound to the primary binding agent, wherein the first linker comprises a first oligonucleotide having a first complementary region;
wherein each buoyant label comprises a second linker bound to the buoyant label; wherein the second linker comprises a second oligonucleotide having a second complementary region,
wherein the second complementary region is perfectly complementary to the first complementary region, and
wherein the processing comprises contacting the target cells and buoyant reagents for a time and under conditions that promote attachment of the cells to one or more of the buoyant reagents by hybridization of the first complementary region to the second complementary region to generate attached target cells;
(b) applying a vectorial force to the host liquid within the functionally closed system to cause the attached target cells to stratify within the host liquid; and
(c) sequestering the attached target cells to an area within the functionally closed system.

2. The cell separation method of claim 1, wherein the buoyant reagents comprise secondary buoyant reagents that assemble within the host liquid, wherein the method further comprises a preprocessing step, prior to step (a), wherein the preprocessing step comprises contacting the host liquid with buoyant labels and binding agents within the functionally wherein the method further comprises: (d) subjecting the attached target cells to a temperature of 37° C. or less within the functionally closed system after step (c) for a time sufficient to dehybridize the first complementary region and the second complementary region to release the buoyant reagents from the target cells.

4. The method of claim 3, wherein the calculated Tm is the Tm as calculated using the nearest-neighbor two-state model:

$$Tm(°C.) = \frac{\Delta H°}{\Delta S° + R\ln[oligo]} - 273.15$$

where $\Delta H°$ (enthalpy) and $\Delta S°$ (entropy) are the melting parameters calculated from the sequence and the published nearest neighbor thermodynamic parameters and under the ionic conditions used, R is the ideal gas constant (1.987 calK$^{-1}$ mole$^{-1}$), [oligo] is the molar concentration of an oligonucleotide, and the constant of −273.15 converts temperature from Kelvin to degrees of Celsius.

5. The method of claim 3, wherein the calculated Tm of the hybrid between the first complementary region and the second complementary region is between 40° C. and about 60° C.

6. The method of claim 1, wherein each buoyant reagent comprises one or more second linkers, wherein the one or more second linkers are bound to one or more first linkers attached to at least one binding agent, wherein the at least one binding agent is capable binding to a cellular epitope on the target cell; and wherein the contacting comprises contacting the target cells and the buoyant reagents for a time and under conditions that promote attachment of the target cells to one or more of the buoyant reagents to generate the attached target cells.

7. The method of claim 1, wherein no intermediate step of removing unbound primary binding agents occurs.

8. The method of claim 1 wherein the method further comprises detaching the buoyant label from the target cells within the functionally closed system to produce detached target cells.

9. The method of claim 1, wherein the target cells and/or the desired cells are selected from the group consisting of tumor cells, cancer stem cells, hematopoietic stem and progenitor cells, mesenchymal stem and progenitor cells, adipose-derived stem and progenitor cells, endothelial progenitor cells found in normal blood, placental/cord blood, bone marrow, white blood cells, granulocytes, mononuclear cells, lymphocytes, monocytes, T-cells, B-cells, NK cells, the stromal vascular fraction cells resident in adipose tissue, cultured cells, genetically modified cells, and sub-populations of such target cells.

10. The method of claim 1, wherein the target cells and/or the desired cells are selected from the group consisting of CD3+ cells, CD4+ cells, CD235a, CD14+, CD19+, CD56+, CD34+, CD117$^+$, KDR$^+$, SIRPA$^+$, ASGR1$^+$, OCLN$^+$, GLUT2$^+$, SLC6A1$^+$, TRA-1-60$^-$, SSEA4$^-$, AP$^-$ (alkaline phosphatase), SSEA3$^-$, TDGF1$^-$, or CD349$^-$ cells.

11. The method of claim 1, wherein the target cells and/or desired cells represent less than 10% of the cells in non-depleted host liquid.

12. The method of claim 1, wherein a recovery efficiency of the desired cells is greater than 68%.

13. The method of claim 1, wherein viability of the desired cells is greater than 90%.

14. The method of claim 1, wherein the target cells and/or desired cells are present at less than 20% of total cells in the host liquid.

15. The method of claim 1 wherein the binding agents are selected from the group consisting of antibodies, oligonucleotides, aptamers, molecularly imprinted polymers, carbohydrates, proteins, peptides, enzymes, small molecules, lipids, fatty acids, metal atoms, metal ions or synthetic polymers.

16. The method of claim 1 wherein the buoyant labels are selected from the group consisting of gas-filled bubbles, hollow polymers, glass beads, microporous beads with entrained gas, droplets of an immiscible liquid, gold nanoparticles, and silver nanoparticles.

17. The method of claim 1 wherein the buoyant labels comprise gas-filled bubbles.

18. The method of claim 17, wherein the gas-filled bubbles have a diameter between about 1 um and about 6.5 um.

19. The method of claim 1, wherein the host liquid is peripheral blood, cord blood, or leukapheresis.

20. A cell separation method, comprising:
(a) providing a host liquid, wherein the host liquid comprises attached target cells, wherein each attached target cell comprises
  (i) a binding agent bound to at least one cellular epitope on a target cell,
  (ii) a first linker bound to the agent, wherein the first linker comprises a first oligonucleotide having a first complementary region;
  (iii) a buoyant label comprising a second linker bound to the buoyant label, wherein the second linker comprises a second oligonucleotide having a second complementary region, wherein the second complementary region is perfectly complementary to the first complementary region, wherein the second complementary region is hybridized to the first complementary region to form a hybrid, and wherein the hybrid of the first and second complementary regions has a calculated Tm of at least 40° C.;
(b) applying a vectorial force, optionally wherein the vectorial force is centrifugation, to the host liquid to cause the attached target cells to stratify within the host liquid;
(c) sequestering the attached target cells; and
(d) subjecting the attached target cells to a temperature of 37° C. or less after step (c) for a time sufficient to dehybridize the first complementary region and the second complementary region to release the buoyant labels from the target cells.

21. The method of claim 1, wherein the buoyant labels comprise gas-filled bubbles and the binding agents comprise antibodies that bind to one or more cellular epitopes on the target cells.

22. The method of claim 21, wherein the gas-filled bubbles have a diameter between about 1 um and about 6.5 um.

23. The method of claim 21, wherein the target cells and/or desired cells represent less than 10% of the cells in non-depleted host liquid, and wherein recovery efficiency of the desired cells is greater than 68%.

24. The method of claim 21, wherein the target cells and/or desired cells represent less than 10% of the cells in non-depleted host liquid, and wherein recovery efficiency of the desired cells is greater than 90%.

25. The method of claim 23, wherein viability of the desired cells is greater than 90%.

26. The method of claim 23, wherein the host liquid is peripheral blood, cord blood, or leukapheresis.

27. The method of claim 26, wherein the desired cells are selected from the group consisting of CD3$^+$, CD4$^+$, CD14+, CD34$^+$ and CD56+ cells.

* * * * *

SEQUENCE LISTING

<160> NUMBER OF SEQ ID NOS: 1

<210> SEQ ID NO 1
<211> LENGTH: 19
<212> TYPE: DNA
<213> ORGANISM: Artificial Sequence
<220> FEATURE:
<223> OTHER INFORMATION: Synthetic

<400> SEQUENCE: 1
ggaagcggtg ctatccatc                                                      19